United States Patent
Piscopio et al.

(10) Patent No.: US 11,739,123 B2
(45) Date of Patent: *Aug. 29, 2023

(54) PROCESS FOR THE PREPARATION OF CYCLIC DEPSIPEPTIDES

(71) Applicant: OnKure, Inc., Boulder, CO (US)

(72) Inventors: Anthony D. Piscopio, Boulder, CO (US); Xiaoyong Fu, Shanghai (CN); Feng Shi, Shanghai (CN); Huayan Liu, Shanghai (CN); Zhifeng Li, Shanghai (CN)

(73) Assignee: OnKure, Inc., Boulder, CO (US)

( * ) Notice: Subject to any disclaimer, the term of this patent is extended or adjusted under 35 U.S.C. 154(b) by 177 days.

This patent is subject to a terminal disclaimer.

(21) Appl. No.: 17/340,731

(22) Filed: Jun. 7, 2021

(65) Prior Publication Data

US 2022/0002347 A1    Jan. 6, 2022

Related U.S. Application Data

(63) Continuation of application No. 16/781,233, filed on Feb. 4, 2020, now Pat. No. 11,053,284, which is a continuation of application No. 16/127,399, filed on Sep. 11, 2018, now Pat. No. 10,689,419, which is a continuation of application No. 15/313,800, filed as application No. PCT/US2015/032590 on May 27, 2015, now Pat. No. 10,100,089.

(60) Provisional application No. 62/003,369, filed on May 27, 2014.

(51) Int. Cl.

| C07K 1/113 | (2006.01) |
|---|---|
| C07K 11/02 | (2006.01) |
| C07K 5/097 | (2006.01) |
| C07D 498/06 | (2006.01) |
| C07D 513/06 | (2006.01) |
| C07D 513/14 | (2006.01) |
| C07K 11/00 | (2006.01) |
| A61K 38/15 | (2006.01) |
| C07K 1/107 | (2006.01) |

(52) U.S. Cl.
CPC .............. *C07K 11/02* (2013.01); *A61K 38/15* (2013.01); *C07D 498/06* (2013.01); *C07D 513/06* (2013.01); *C07D 513/14* (2013.01); *C07K 1/1077* (2013.01); *C07K 1/113* (2013.01); *C07K 5/0821* (2013.01); *C07K 11/00* (2013.01)

(58) Field of Classification Search
CPC .......... A61K 38/15; C07K 1/02; C07K 1/113; C07K 1/1077; C07K 11/00; C07K 11/02
See application file for complete search history.

(56) References Cited

U.S. PATENT DOCUMENTS

| 8,933,195 B2 | 1/2015 | Jiang et al. |
|---|---|---|
| 10,100,089 B2 | 10/2018 | Piscopio et al. |
| 10,689,419 B2 | 6/2020 | Piscopio et al. |
| 11,053,284 B2 * | 7/2021 | Piscopio ................ A61P 43/00 |
| 2008/0234265 A1 | 9/2008 | Witta et al. |
| 2010/0029731 A1 | 2/2010 | Williams et al. |
| 2011/0092697 A1 | 4/2011 | Luesch et al. |
| 2012/0264794 A1 | 10/2012 | Williams et al. |

(Continued)

FOREIGN PATENT DOCUMENTS

| CN | 101175492 A | 5/2008 |
|---|---|---|
| CN | 101781321 A | 7/2010 |

(Continued)

OTHER PUBLICATIONS

Chinese Office Action for Chinese Application No. 201910227308.2, dated Jul. 5, 2022, with translation, 12 pages.

(Continued)

*Primary Examiner* — Jeffrey E. Russel
(74) *Attorney, Agent, or Firm* — RatnerPrestia

(57) ABSTRACT

Processes for preparing compounds of Formula (1) and Formula (2) are described, wherein X, Y, Z, $R_1$-$R_7$, L and n are defined herein. Intermediates useful in the preparation of the compounds of Formula (1) and Formula (2) are also described.

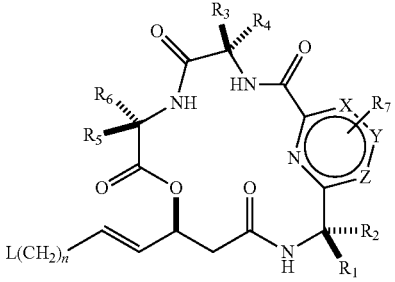

Formula (1)

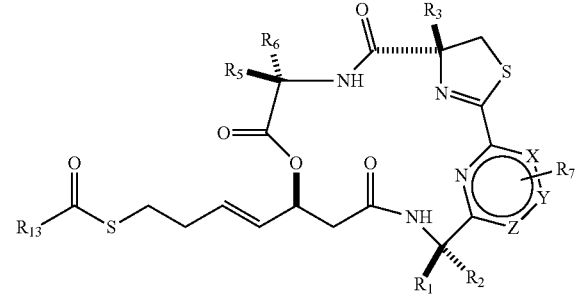

Formula (2)

9 Claims, 1 Drawing Sheet

(56) References Cited

U.S. PATENT DOCUMENTS

2013/0203681 A1    8/2013    Liu et al.
2014/0243501 A1    8/2014    Jiang et al.

FOREIGN PATENT DOCUMENTS

| | | |
|---|---|---|
| CN | 103232474 A | 4/2013 |
| JP | 2013528182 A | 7/2013 |
| WO | 2010009334 A1 | 1/2010 |
| WO | 2011150283 A1 | 12/2011 |
| WO | 2013071715 A1 | 5/2013 |

OTHER PUBLICATIONS

Benelkebir et al., "Total Synthesis of Largazole and Analogues: HDAC Inhibition, Antiproliferative Activity and Metabolic Stability," Bioorganic & Medicinal Chemistry, Jun. 15, 2011, vol. 19(12), pp. 3650-3658. 201.

Berge et al., "Pharmaceutical Salts", Journal of Pharmaceutical Sciences, vol. 66, No. 1, Jan. 1977, 19 pages.

Bhansali et al., "Largazole and Analogues with Modified Metal-Binding Motifs Targeting Histone Deacetylases: Synthesis and Biological Evaluation", J. Med. Chem., 54:7453-7463 (2011).

Bowers et al., "Total synthesis and biological mode of action of largazole: a potent class I histone deacetylase inhibitor", J. Am. Chem. Soc., 130(33), 2008, 11219-11222.

Chinese Office Action for Chinese Application No. 201580027121.8, dated Apr. 27, 2018, 10 pages.

Extended European Search Report for European Application No. 15800006.7, dated Dec. 8, 2017, 9 pages.

Extended European Search Report for European Application No. 19185579.0, dated Sep. 23, 2019, 7 pages.

Guerra-Bubb et al., "Synthesis and HDAC Inhibitory Activity of Isosteric-thiazoline-oxazole Largazole Analogs", Bioorganic & Medicinal Chemistry Letters, 23:6025-5028 (2013).

Hong et al., "Largazole: From Discovery to Broad-spectrum Therapy", Nat. Prod. Rep., 29:449-456 (2012). 2021.

International Search Report and Written Opinion for International Application No. PCT/US2015/032590, dated Aug. 14, 2015, 7 pages.

Japanese Decision of Refusal for Japanese Application No. 2019-044425, dated Sep. 15, 2020, with translation, 6 pages.

Japanese Decision of Rejection for Japanese Application No. 2019-2044425, dated Sep. 15, 2020, 3 pages.

Japanese Office Action for Japanese Application No. 2017-514999, dated Oct. 31, 2017, 4 pages.

Japanese Office Action for Japanese Application No. 2017-514999, dated Sep. 18, 2019, 4 pages.

Japanese Office Action for Japanese Application No. 2019-044425, dated Feb. 4, 2020, 6 pages.

Kiick et al., "Incorporation of azides into recombinant proteins for chemoselective modification by the Staudinger Ligation", Proc. Natl. Acad. Sci. U.S.A. 99(1), 2002: 19-24.

Lemieux et al., "Chemoselective Ligation Reactions with Proteins, Oligosaccharides and Cells", Reviews, 1998, vol. 16, pp. 506-513. (Abstract only).

Nasveschuk et al., "A Concise Total Synthesis of Largazole, Solution Structure, and Some Preliminary Structure Activity Relationships", Organic Letters, 2008, vol. 10, No. 16, pp. 3595-3598.

Rautio et al., "Prodrugs: design and clinical applications", Nat. Rev. Drug Discov. 7(3), 2008: 255-270.

Ren et al., "Total Synthesis of Largazole", Synlett, 15:2379-2383 (2008).

Seiser et al., "Synthesis and Biological Activity of Largazole and Derivatives", Angew. Chem. Int. Ed., 2008, vol. 47, pp. 6483-6485.

Souto et al., "Synthesis and Biological Characterization of the Histone Deacetylase Inhibitor Largazole and C7-Modified Analogues", J. Med. Chem., 53(12):4654-4667 (2010).

Taiwanese Office Action for Taiwanese Application No. 104117108, dated Apr. 22, 2019, 7 pages.

Taiwanese Office Action for Taiwanese Application No. 108116572, dated Mar. 2, 2020, 6 pages.

Voigtritter et al., "Rate Enhanced Olefin Cross-Metathesis Reactions: The Copper Iodide Effect", J. Org. Chem., 76(11):4697-4702 (2011).

Xiao et al., "Concise Total Synthesis of Largazole", Journal of Asian Natural Products Research, 12(11):940-949 (2010).

Ying et al., "Total Synthesis and Molecular Target of Largazole, a Histone Deacetylase Inhibitor", Journal of American Cancer Society, 2008, vol. 130, pp. 8455-8459.

Zeng et al., "Total Synthesis and Biological Evaluation of Largazole and Derivatives with Promising Selectivity for Cancers Cells", Organic Letters, vol. 12. No. 6, pp. 1368-1371. (2010).

Entire patent prosecution history of U.S. Appl. No. 15/313,800, filed, Nov. 23, 2016, entitled, "Process for the Preparation of Cyclic Depsipeptides".

Entire patent prosecution history of U.S. Appl. No. 16/127,399, filed, Sep. 11, 2018, entitled, "Process for the Preparation of Cyclic Depsipeptides".

Entire patent prosecution history of U.S. Appl. No. 16/781,233, filed, Feb. 4, 2020, entitled, "Process for the Preparation of Cyclic Depsipeptides".

Taiwanese Office Action with Search Report for Taiwanese Application No. 109138257, dated Jan. 11, 2022, with translation, 7 pages.

\* cited by examiner

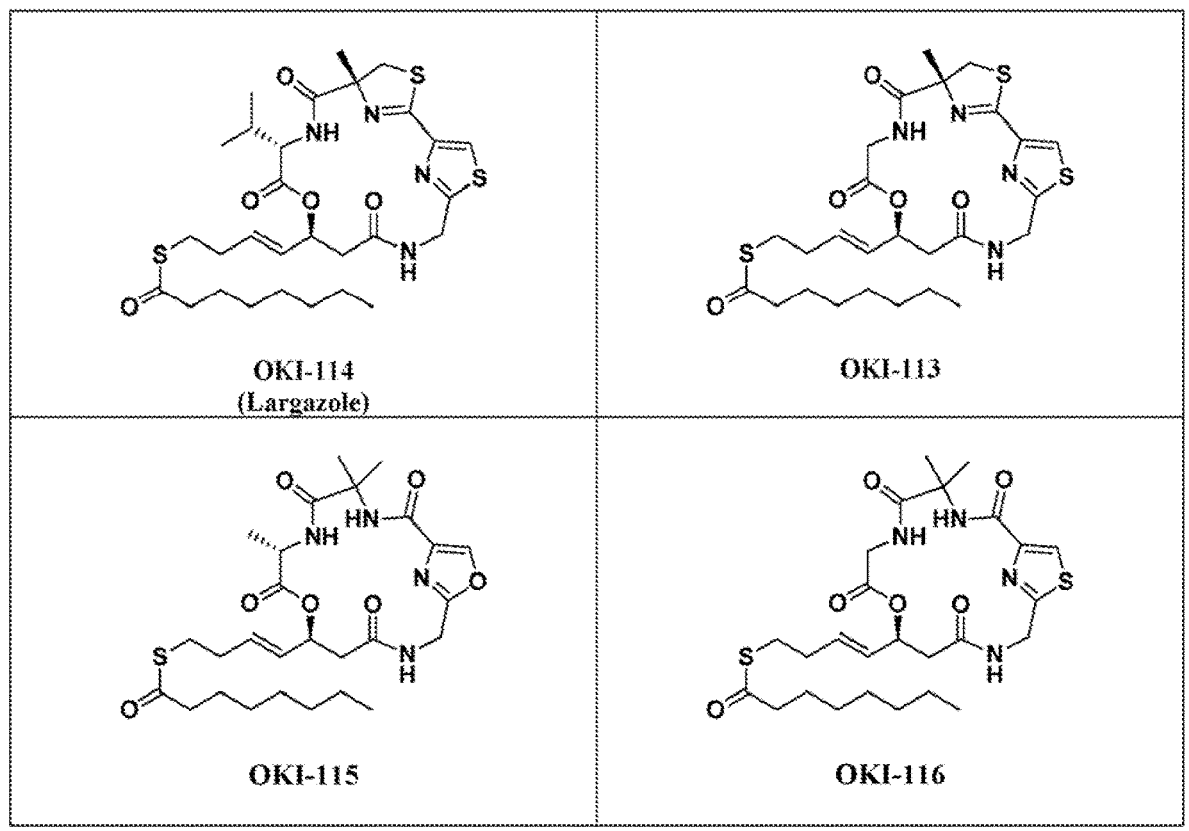

PROCESS FOR THE PREPARATION OF CYCLIC DEPSIPEPTIDES

CROSS-REFERENCE TO RELATED APPLICATIONS

This application is a Continuation of U.S. application Ser. No. 16/781,233, filed Feb. 4, 2020 (allowed) which is a Continuation of application Ser. No. 16/127,399, filed Sep. 11, 2018 (now U.S. Pat. No. 10,689,419, issued Jun. 23, 2020) which is a Continuation of U.S. application Ser. No. 15/313,800, filed Nov. 23, 2016 (now U.S. Pat. No. 10,100,089, issued Oct. 16, 2018) which is the national phase of International Application No PCT/US2015/32590, filed May 27, 2015, which claims the benefit of priority to U.S. Provisional Application No. 62/003,369, filed May 27, 2014.

BACKGROUND OF THE INVENTION

The invention relates to the preparation of substituted, cyclic depsipeptides and to intermediates useful in their preparation. The cyclic depsipeptides prepared as described herein are disclosed in WO/2011/150283, which is incorporated by reference in its entirety.

The cyclic depsipeptides prepared in accord with the present invention are known to be histone deacetylase (HDAC) inhibitors as disclosed in, for example, U.S. 20130203681 and are known to be useful in the treatment of diseases mediated by HDAC disregulation, such as cancer, inflammatory diseases, autoimmune diseases, allergic diseases and diseases of the central nervous system.

SUMMARY OF THE INVENTION

An aspect of the present invention relates to a process of preparing a compound of the Formula (1)

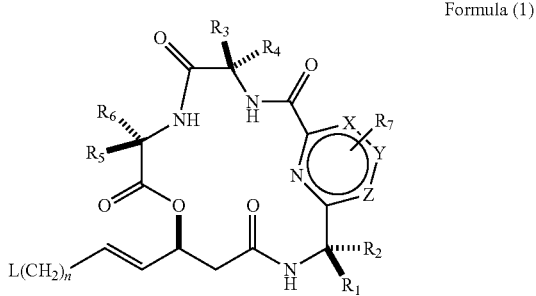

Formula (1)

or a pharmaceutically acceptable salt thereof,
wherein:

X, Y and Z are independently carbon or nitrogen, or alternatively, Y is a direct bond and X and Z are independently carbon, nitrogen, oxygen or sulfur;

$R_1$ and $R_2$ are independently selected from the group consisting of H, $C_1$-$C_{10}$ alkyl and $C_3$-$C_7$ cycloalkyl, or $R_1$ and $R_2$ taken together form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, $NR_8C(O)OR_9$, —$NR_8CO_2R_9$, and —$C(O)NR_8R_9$;

$R_3$ and $R_4$ are independently selected from the group consisting of H, $C_1$-$C_{10}$ alkyl and $C_3$-$C_7$ cycloalkyl, or $R_3$ and $R_4$ taken together form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, $NR_8C(O)OR_9$, —$NR_8CO_2R_9$, and —$C(O)NR_8R_9$;

$R_5$ and $R_6$ are independently selected from the group consisting of H, $C_1$-$C_{10}$ alkyl and $C_3$-$C_7$ cycloalkyl, or $R_5$ and $R_6$ taken together form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, $NR_8C(O)OR_9$, —$NR_8CO_2R_9$, and —$C(O)NR_8R_9$;

$R_7$ is independently selected from the group consisting of H, $C_1$-$C_{10}$ alkyl, $C_3$-$C_7$ cycloalkyl and $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, $NR_8C(O)OR_9$, —$NR_8CO_2R_9$ and —$C(O)NR_8R_9$;

$R_8$ and $R_9$ are independently selected from the group consisting of H, $C_1$-$C_{10}$ alkyl and $C_3$-$C_7$ cycloalkyl, or $R_8$ and $R_9$ taken together form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_{10}R_{11}$, —$NR_{10}C(O)R_{11}$, —$NR_{10}C(O)OR_{11}$ and —$C(O)NR_{10}R_{11}$;

$R_{10}$ and $R_{11}$ are independently selected from the group consisting of H, $C_1$-$C_{10}$ alkyl and $C_3$-$C_7$ cycloalkyl, or $R_{10}$ and $R_{11}$ taken together form a $C_3$-$C_7$ cycloalkyl or $C_3$-$C_7$ heterocycloalkyl;

L is Cl or $SR_{12}$;

$R_{12}$ is independently selected from the group consisting of H, triphenylmethyl, $C(O)R_{13}$, $CO_2R_{13}$, $C(O)NR_{13}R_{14}$, $C(O)CR_{13}R_{14}NR_{13}R_{14}$, amino acid, $P(O)(OR_{15})_2$ and $SR_{16}$;

$R_{13}$ and $R_{14}$ are independently selected from the group consisting of H, $C_1$-$C_{10}$ alkyl, $C_3$-$C_7$ cycloalkyl, $C_3$-$C_7$ heterocycloalkyl, aryl and heteroaryl, or $R_{13}$ and $R_{14}$ taken together form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_{10}R_{11}$ and —$NR_{10}C(O)R_{11}$, wherein $R_{10}$ and $R_{11}$ are defined as above;

$R_{15}$ is tert-butyl or $-(CH_2)_2Si(CH_3)_3$;
$R_{16}$ is $C_1$-$C_{10}$ alkyl or $C_3$-$C_7$ cycloalkyl;
n is 2 or 3, comprising:
  converting alcohol (VI-A)

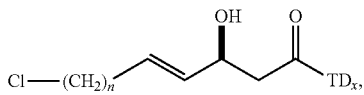

(VI-A)

wherein TDx is a chiral auxiliary,
to carbamate (VIII-A)

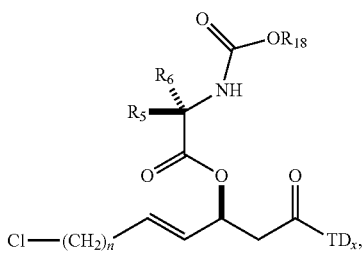

(VIII-A)

wherein $R_{18}$ is selected from the group consisting of $-CH_2CH_2Si(CH_3)_3$, (9H-fluoren-9-yl)methyl and tert-butyl; and n, $R_5$, $R_6$ and TDx are defined as above;
by reaction of alcohol (VI-A) with protected amino acid (VII)

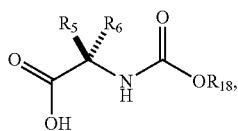

(VII)

wherein $R_5$, $R_6$ and $R_{18}$ are as defined above, followed by
reacting carbamate (VIII-A) with heterocyclic compound (IX)

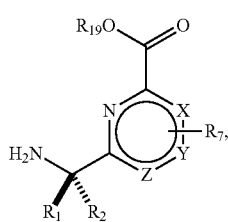

(IX)

wherein $R_{19}$ is selected from the group consisting of $-CH_2CH_2Si(CH_3)_3$, (9H-fluoren-9-yl)methyl and tert-butyl; and n, X, Y and Z are as defined above, to provide compound (X-A)

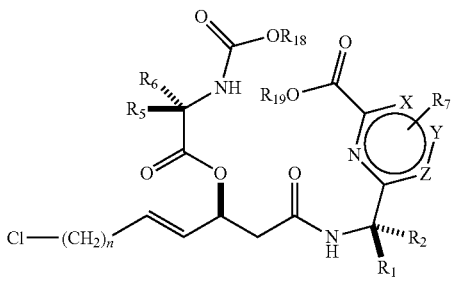

(X-A)

wherein n, $R_1$, $R_2$, $R_5$, $R_6$, $R_7$, $R_{18}$, $R_{19}$, X, Y and Z are as defined above, followed by
selectively removing the carbamate protecting group from compound (X-A) to provide amine (XVII-A)

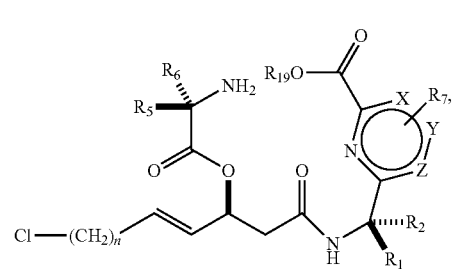

(XVII-A)

wherein n, $R_1$, $R_2$, $R_5$, $R_6$, $R_7$, $R_{19}$, X, Y and Z are as defined above, followed by
reacting compound (XVII-A) with protected amino acid (VII-A)

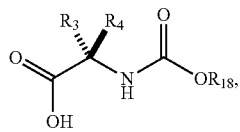

(VII-A)

wherein $R_3$, $R_4$ and $R_{18}$ are as defined above,
to provide amide (XVIII-A)

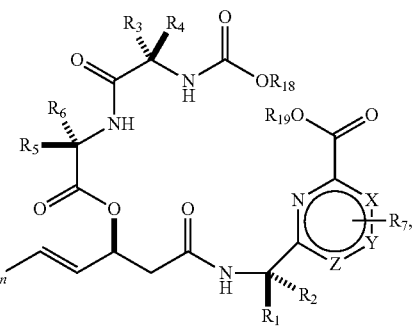

(XVIII-A)

wherein n, $R_1$ to $R_7$, $R_{18}$, $R_{19}$, X, Y and Z are as defined above, followed by deprotecting amide (XVIII-A) to compound (XIX-A)

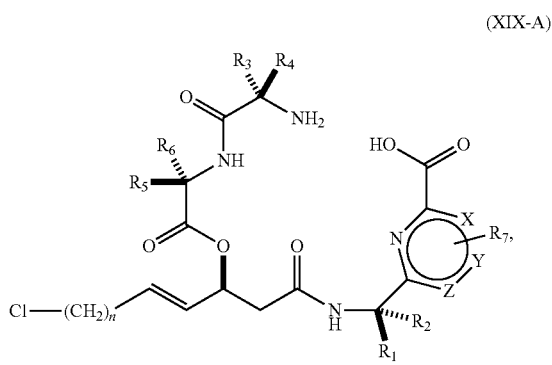
(XIX-A)

wherein n, $R_1$ to $R_7$, X, Y and Z are as defined above, followed by ring closure to compound (XX-A)

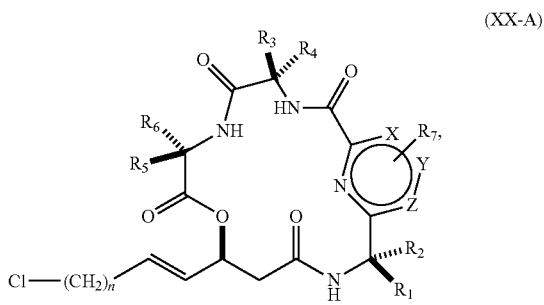
(XX-A)

wherein n, $R_1$ to $R_7$, X, Y and Z are as defined above, followed by reacting (XX-A) with $R_{12}$—SH to provide a compound of Formula (1).

In an aspect of the invention,

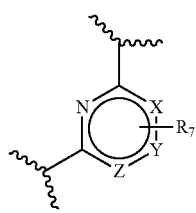

is a thiazole or an oxazole.

In an aspect of the invention, $R_5$ is H and $R_6$ is selected from the group consisting of H, isopropyl and methyl.

In an aspect of the invention, $R_5$ is H and $R_6$ is isopropyl.

In an aspect of the invention, $R_{12}$ is C(O)$C_7$alkyl.

In an aspect of the invention, $R_{12}$ is C(O)(CH$_2$)CH$_3$.

In an aspect of the invention, $R_3$ and $R_4$ are methyl.

In an aspect of the invention, the compound of Formula (1) is

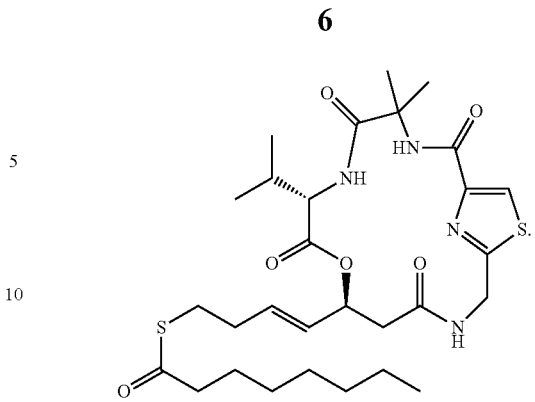

In an aspect of the invention, the compound of Formula (1) is

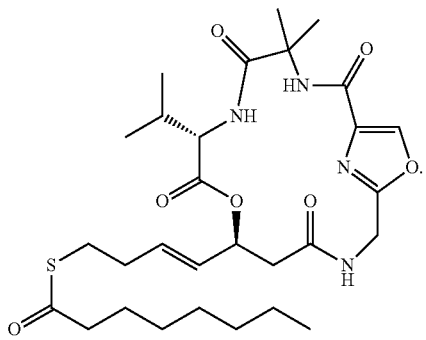 [SMILES: CCCCCCCC(=O)SCC/C=C/[C@@H]1CC(=O)NCc2nc(co2)C(=O)NC(C)(C)C(=O)N[C@@H](C(C)C)C(=O)O1]

In an aspect of the invention, $R_{12}$ is C(O) $CR_{13}R_{14}NR_{13}R_{14}$.

An aspect of the present invention relates to a process of preparing a compound of the Formula (2)

Formula (2)
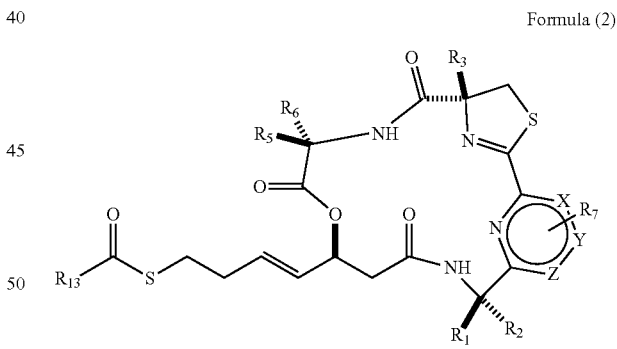

or a pharmaceutically acceptable salt thereof,
wherein:
X, Y and Z are independently carbon or nitrogen, or alternatively, Y is a direct bond and X and Z are independently carbon, nitrogen, oxygen or sulfur;
$R_1$ and $R_2$ are independently selected from the group consisting of H, $C_1$-$C_{10}$ alkyl and $C_3$-$C_7$ cycloalkyl, or $R_1$ and $R_2$ taken together form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_8$R$_9$, —NR$_8$C(O)R$_9$, —NR$_8$C(O)OR$_9$, —NR$_8$CO$_2$R$_9$, and —C(O)NR$_8$R$_9$;

R$_3$ is selected from the group consisting of H, C$_1$-C$_{10}$ alkyl and C$_3$-C$_7$ cycloalkyl, or R$_3$ and R$_4$ taken together form a C$_3$-C$_7$ cycloalkyl or C$_3$-C$_7$ heterocycloalkyl wherein the C$_1$-C$_{10}$ alkyl, C$_3$-C$_7$ cycloalkyl and C$_3$-C$_7$ heterocycloalkyl are optionally substituted with one or more substituents selected from the group consisting of C$_1$-C$_{10}$ alkyl, C$_3$-C$_7$ cycloalkyl, C$_3$-C$_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_8$R$_9$, —NR$_8$C(O)R$_9$, NR$_8$C(O)OR$_9$, —NR$_8$CO$_2$R$_9$, and —C(O)NR$_8$R$_9$;

R$_5$ and R$_6$ are independently selected from the group consisting of H, C$_1$-C$_{10}$ alkyl and C$_3$-C$_7$ cycloalkyl, or R$_5$ and R$_6$ taken together form a C$_3$-C$_7$ cycloalkyl or C$_3$-C$_7$ heterocycloalkyl wherein the C$_1$-C$_{10}$ alkyl, C$_3$-C$_7$ cycloalkyl and C$_3$-C$_7$ heterocycloalkyl are optionally substituted with one or more substituents selected from the group consisting of C$_1$-C$_{10}$ alkyl, C$_3$-C$_7$ cycloalkyl, C$_3$-C$_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_8$R$_9$, —NR$_8$C(O)R$_9$, —NR$_8$C(O)OR$_9$, —NR$_8$CO$_2$R$_9$ and —C(O)NR$_8$R$_9$;

R$_7$ is independently selected from the group consisting of H, C$_1$-C$_{10}$ alkyl, C$_3$-C$_7$ cycloalkyl and C$_3$-C$_7$ heterocycloalkyl wherein the C$_1$-C$_{10}$ alkyl, C$_3$-C$_7$ cycloalkyl and C$_3$-C$_7$ heterocycloalkyl are optionally substituted with one or more substituents selected from the group consisting of C$_1$-C$_{10}$ alkyl, C$_3$-C$_7$ cycloalkyl, C$_3$-C$_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_8$R$_9$, —NR$_8$C(O)R$_9$, —NR$_8$C(O)OR$_9$, —NR$_8$CO$_2$R$_9$ and —C(O)NR$_8$R$_9$;

R$_8$ and R$_9$ are independently selected from the group consisting of H, C$_1$-C$_{10}$ alkyl and C$_3$-C$_7$ cycloalkyl, or R$_8$ and R$_9$ taken together form a C$_3$-C$_7$ cycloalkyl or C$_3$-C$_7$ heterocycloalkyl wherein the C$_1$-C$_{10}$ alkyl, C$_3$-C$_7$ cycloalkyl and C$_3$-C$_7$ heterocycloalkyl are optionally substituted with one or more substituents selected from the group consisting C$_1$-C$_{10}$ alkyl, C$_3$-C$_7$ cycloalkyl, C$_3$-C$_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_{10}$R$_{11}$, —NR$_{10}$C(O)R$_{11}$, —NR$_{10}$C(O)OR$_{11}$ and —C(O)NR$_{10}$R$_{11}$;

R$_{10}$ and R$_{11}$ are independently selected from the group consisting of H, C$_1$-C$_{10}$ alkyl and C$_3$-C$_7$ cycloalkyl, or R$_{10}$ and R$_{11}$ taken together form a C$_3$-C$_7$ cycloalkyl or C$_3$-C$_7$ heterocycloalkyl; and R$_{13}$ is selected from the group consisting of C$_1$-C$_{10}$ alkyl, C$_3$-C$_7$ cycloalkyl, C$_3$-C$_7$ heterocycloalkyl, aryl and heteroaryl, wherein the C$_1$-C$_{10}$ alkyl, C$_3$-C$_7$ cycloalkyl and C$_3$-C$_7$ heterocycloalkyl are optionally substituted with one or more substituents selected from the group consisting of C$_1$-C$_{10}$ alkyl, C$_3$-C$_7$ cycloalkyl, C$_3$-C$_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_{10}$R$_{11}$ and —NR$_{10}$C(O)R$_{11}$, wherein R$_{10}$ and R$_{11}$ are defined as above, comprising reacting carbamate (VIII)

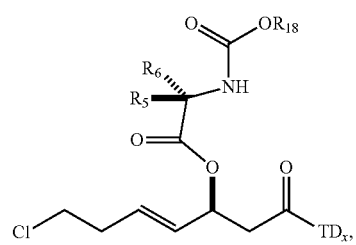

(VIII)

wherein R$_{18}$ is selected from the group consisting of —CH$_2$CH$_2$Si(CH$_3$)$_3$, (9H-fluoren-9-yl)methyl and tert-butyl; TDx is a chiral auxiliary; and R$_5$ and R$_6$ are defined as above, with heterocyclic compound (XXVI)

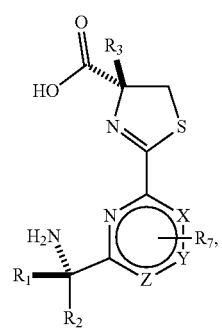

(XXVI)

wherein R$_1$, R$_2$, R$_3$, R$_7$, X, Y and Z are as defined above, to provide compound (XXVII)

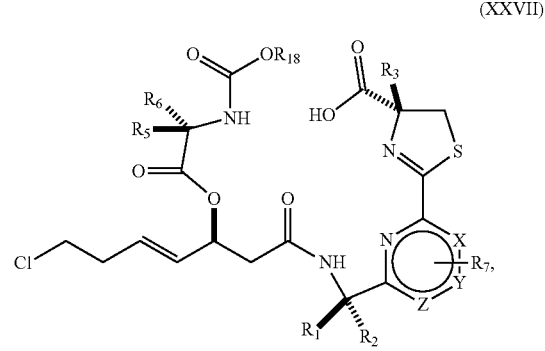

(XXVII)

wherein R$_1$, R$_2$, R$_3$, R$_5$, R$_6$, R$_7$, R$_{18}$, X, Y and Z are as defined above, followed by removing the carbamate protecting group from compound (XXVII) to provide amine (XXVII)

(XXVIII)

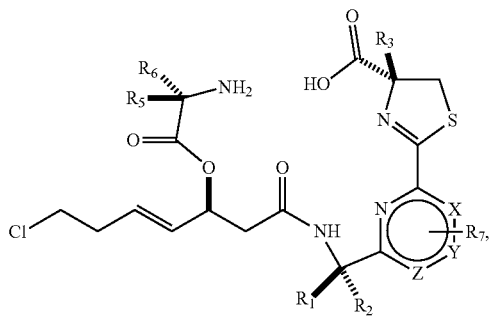

wherein $R_1$, $R_2$, $R_3$, $R_5$, $R_6$, $R_7$, X, Y and Z are as defined above, followed by
ring closure to provide amide (XXIX)

(XXIX)

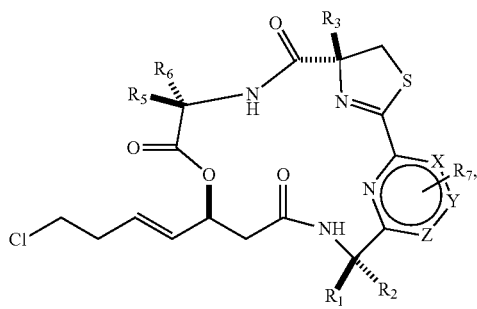

wherein $R_1$, $R_2$, $R_3$, $R_5$, $R_6$, $R_7$, X, Y and Z are as defined above, followed by
reacting (XXIX) with $R_{13}$—SH (XXI)

(XXI)

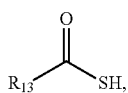

wherein $R_{13}$ is as defined above,
to provide a compound of Formula (2).
In an aspect of the invention to prepare a compound of Formula (2),

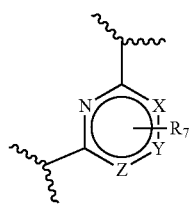

is a thiazole.
In an aspect of the invention to prepare a compound of Formula (2), $R_5$ is H and $R_6$ is isopropyl.
In an aspect of the invention to prepare a compound of Formula (2), $R_{13}$ is —(CH$_2$)$_6$CH$_3$.
In an aspect of the invention to prepare a compound of Formula (2), $R_1$ and $R_2$ are H.

In an aspect of the invention to prepare a compound of Formula (2), the compound of Formula (2) is

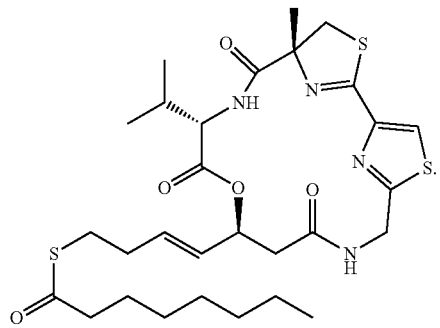 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)O1]

BRIEF DESCRIPTION OF THE DRAWINGS

FIG. 1 depicts the chemical structures of largazole and several analogs of largazole.

DETAILED DESCRIPTION

A "moiety" or "group" is any type of molecular arrangement designated by formula, chemical name, or structure. Within the context of certain embodiments, a conjugate is said to comprise one or more moieties or chemical groups. This means that the formula of the moiety is substituted at some place in order to be joined and be a part of the molecular arrangement of the conjugate. Although moieties may be directly covalently joined, it is not intended that the joining of two or more moieties must be directly to each other. A linking group, crosslinking group, or joining group refers to any molecular arrangement that will connect the moieties by covalent bonds such as, but not limited to, one or more amide group(s), which may join the moieties. Additionally, although the conjugate may be unsubstituted, the conjugate may have a variety of additional substituents connected to the linking groups and/or connected to the moieties.

A "polymer" or "polymer group" refers to a chemical species or group made up of repeatedly linked moieties. Within certain embodiments, it is preferred that the number of repeating moieties is three or more or greater than 10. The linked moieties may be identical in structure or may have variation of moiety structure. A "monomeric polymer" or "homopolymer" is a polymer that contains the same repeating, asymmetric subunit. A "copolymer" is a polymer that is derived from two or more types of monomeric species, i.e., two or more different chemical asymmetric subunits. "Block copolymers" are polymers comprised of two or more species of polymer subunits linked by covalent bonds.

The term "substituted", as used herein, refers to the replacement of at least one hydrogen atom of a molecular arrangement with a substituent. In the case of an oxo substituent ("=O"), two hydrogen atoms are replaced. When substituted, one or more of the groups below are "substituents." Substituents include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocyclyl, and heterocyclealkyl, as well as, —NRaRb, —NRaC(O)Rb, —NRaC(O)NRaNRb, —NRaC(=O)ORb, —NRaSO$_2$Rb, —C(=O)

Ra, —C(=O)ORa, —C(=O)NRaRb, —OC(=O)NRaRb, —ORa, —SRa, —SORa, —S(=O)₂Ra, —OS(=O)₂Ra and —S(=O)ORa.

In addition, the above substituents may be further substituted with one or more of the above substituents, such that the substituent comprises a substituted alkyl, substituted aryl, substituted arylalkyl, substituted heterocycle, or substituted heterocycloalkyl. Ra and Rb in this context may be the same or different and, independently, hydrogen, alkyl, haloalkyl, substituted alkyl, aryl, substituted aryl, arylalkyl, substituted arylalkyl, heterocyclyl, substituted heterocyclyl, heterocycloalkyl or substituted heterocycloalkyl.

The term "unsubstituted", as used herein, refers to any compound that does not contain extra substituents attached to the compound. An unsubstituted compound refers to the chemical makeup of the compound without extra substituents, e.g., the compound does not contain protecting group (s). For example, unsubstituted proline is a proline amino acid even though the amino group of proline may be considered disubstituted with alkyl groups.

The term "alkyl", as used herein, refers to any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 7 to 10 carbon atoms. Representative saturated straight chain alkyls include, but are not limited to, methyl, ethyl, n-propyl, n-butyl, n-pentyl, n-hexyl, n-heptyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, refers to any aromatic carbocyclic moiety such as, but not limited to, phenyl or naphthyl.

The term "arylalkyl", or "aralkyl" as used herein, refers to any alkyl having at least one alkyl hydrogen atom replaced with an aryl moiety, such as, but not limited to, benzyl, —(CH₂)₂-phenyl, —(CH₂)₃-phenyl, —CH(phenyl)₂, and the like.

The term "halogen", as used herein, refers to any fluoro, chloro, bromo, or iodo moiety.

The term "haloalkyl", as used herein, refers to any alkyl having at least one hydrogen atom replaced with halogen, such as trifluoromethyl, and the like.

The term "heteroaryl", as used herein, refers to any aromatic heterocycle ring of 5 to 10 members and having at least one heteroatom selected from nitrogen, oxygen and sulfur, and containing at least 1 carbon atom, including, but not limited to, both mono and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl", as used herein, refers to any alkyl having at least one alkyl hydrogen atom replaced with a heteroaryl moiety, such as —CHpyridinyl, —CH₂pyrimidinyl, and the like.

The term "heterocycle" or "heterocyclic ring", as used herein, refers to any 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocycloalkyl", as used herein, refers to any alkyl having at least one alkyl hydrogen atom replaced with a heterocycle, such as —CH₂-morpholinyl, and the like.

The term "homocycle" or "cycloalkyl", as used herein, refers to any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, refers to at least one alkyl moiety attached through a nitrogen bridge (e.g., —N-alkyl or —N-(alkyl)-N—) including, but not limited to, methylamino, ethylamino, dimethylamino, diethylamino, and the like.

The term "alkyloxy" or "alkoxy", as used herein, refers to any alkyl moiety attached through an oxygen bridge (e.g., —O-alkyl) such as, but not limited to, methoxy, ethoxy, and the like.

The term "alkylthio", as used herein, refers to any alkyl moiety attached through a sulfur bridge (e.g., —S-alkyl) such as, but not limited to, methylthio, ethylthio, and the like.

The term "alkenyl" refers to an unbranched or branched hydrocarbon chain having one or more double bonds therein. The double bond of an alkenyl group can be unconjugated or conjugated to another unsaturated group. Suitable alkenyl groups include, but are not limited to vinyl, allyl, butenyl, pentenyl, hexenyl, butadienyl, pentadienyl, hexadienyl, 2-ethylhexenyl, 2-propyl-2-butenyl,4-(2-methyl-3-butene)-pentenyl. An alkenyl group can be unsubstituted or substituted with one or two suitable substituents.

The term "alkynyl" refers to unbranched or branched hydrocarbon chain having one or more triple bonds therein. The triple bond of an alkynyl group can be unconjugated or conjugated to another unsaturated group. Suitable alkynyl groups include, but are not limited to ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or two suitable substituents.

The term "salts", as used herein, refers to any salt, such as a pharmaceutically acceptable salt, that complexes with identified compounds contained herein. Examples of such salts include, but are not limited to, acid addition salts formed with inorganic acids (e.g., hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known by a person skilled in the art, which specifically include the quaternary ammonium salts of the formula —NR,R',R"$^+$Z$^-$, wherein each R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the term "prodrug" refers to a derivative of a compound that can hydrolyze, oxidize, or otherwise react under biological conditions (i vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention, and/or their salts when salt formation is possible, but in particular, derivatives of zinc binding thiol moiety. Examples of prodrug moieties include substituted and unsubstituted, branched or unbranched lower alkyl ester moieties (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), heteroaryl esters (nicotinate ester), substituted (e.g., with methyl, halo, or methoxy substituents) aryl and aryl-lower alkyl esters, amides, lower-alkyl amides, di-lower alkyl amides, and hydroxy amides.

Naturally occurring amino acid esters or their enantiomers, dipeptide esters, phosphate esters, methoxyphosphate esters, disulfides and disulfide dimers. Prodrugs and their uses are well known in the art (see, e.g., Berge et al., Pharmaceutical Salts, *J. Pharm. Sci.* 66, 1-19 (1977)). Prodrugs can typically be prepared using well-known methods, such as those described in *Burger's Medicinal Chemistry and Drug Discovery* (Manfred E. Wolff ed. (1995)) and (Rautio, *Nat. Rev. Drug Discov.* 7, 255-270 (2008)).

As used herein, "reactive groups" refer to nucleophiles, electrophiles, or radically active groups, i.e., groups that react in the presence of radicals. A nucleophile is a moiety that forms a chemical bond to its reaction partner (the electrophile) by donating both bonding electrons.

Electrophiles accept these electrons. Nucleophiles may take part in nucleophilic substitution, whereby a nucleophile becomes attracted to a full or partial positive charge on an element and displaces the group it is bonded to. Alternatively nucleophiles may take part in substitution of carbonyl group. Carboxylic acids are often made electrophilic by creating succinyl esters and reacting these esters with aminoalkyls to form amides. Other common nucleophilic groups include thiolalkyls, hydroxylalkyls, primary and secondary amines, and carbon nucleophiles such as enols and alkyl metal complexes. Other preferred methods of ligating proteins, oligosaccharides and cells using reactive groups are disclosed in (Lemieux and Bertozzi (1998)), incorporated herein by reference. In yet another preferred method, one provides reactive groups for the Staudinger ligation, i.e., "click chemistry" with an azide comprising moiety and alkynyl reactive groups to form triazoles. Michael additions of a carbon nucleophile enolate with an electrophilic carbonyl, or the Schiff base formation of a nucleophilic primary or secondary amine with an aldehyde or ketone may also be utilized. Other methods of bioconjugation are provided in (Hang and Bertozzi, *J. Am. Chem Soc.* 123, 1242-1243 (2001)) and (Kiick et al. (2002)), both of which are incorporated by reference in their entireties.

The processes of the present invention used to prepare the compounds of the present invention, such as those represented by Formula (1) and Formula (2) are illustrated in the following schemes. Unless otherwise indicated, the variables $R_1$-$R_{21}$, X, Y, Z, M, $TD_x$, and n are defined as above. In particular, the schemes and discussions that follow describe the preparation of the compounds represented by formulae I to XXIX.

The reaction described in Step 1 of Scheme 1 involves a ruthenium carbene-catalyzed cross olefin metathesis reaction between Compound I and Compound II to produce Compound III and is performed under conditions that are analogous to those described in Voigtritter, K. et al., *J. Org. Chem.* 76, 4697-4702 (2011).

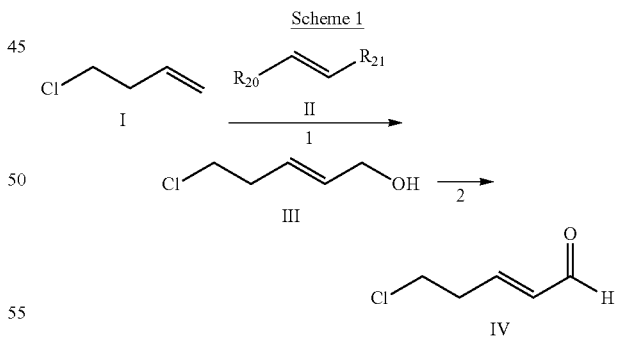

In particular, when Compound I was reacted with Compound II (an allyl alcohol where $R_{20}$ is H and $R_{21}$ is $CH_2OH$, or $R_{20}$ and $R_{21}$ are both $CH_2OH$) in the presence of a ruthenium carbene catalyst such as, but not limited to, benzylidene-bis(tricyclohexylphosphine)dichlororuthenium (Grubbs first generation catalyst), (1,3-bis(2,4,6-trimethylphenyl)-2-imidazolidinylidene)dichloro(phenylmethylene)(tricyclohexylphosphine)ruthenium (Grubbs second generation catalyst), (1,3-bis-(2,4,6-trimethylphenyl)-2-imidazolidinylidene)dichloro(o-isopropoxyphenylmethylene)

ruthenium (Hoveyda-Grubbs catalyst), or 1,3-bis(2,4,6-trimethylphenyl)-4,5-dihydroimidazol-2-ylidene[2-(i-propoxy)-5-(N,N-dimethylaminosulfonyl)phenyl] methylene ruthenium(II) dichloride (Zhan catalyst 1B), in an amount ranging from about 0.1 mol % to about 5 mol %, preferably about 0.5 mol %, in combination with copper (I) iodide in an amount ranging from about 1 mol % to about 20 mol %, preferably about 6 mol %, in a solvent such as, but not limited to, dichloromethane, 1,2-dichloroethane, diethyl ether, methyl tert-butyl ether, diisopropyl ether, di-n-butyl ether, tetrahydrofuran or toluene, preferably dichloromethane, at a temperature range of about 0° C. to about 100° C., preferably at room temperature (about 25° C.), Compound III ((E)-5-chloropent-2-en-1-ol), was obtained and used directly in the next step.

As described in Step 2 of Scheme 1, Compound III ((E)-5-chloropent-2-en-1-ol) was oxidized to the corresponding aldehyde, Compound IV ((E)-5-chloropent-2-enal) by treatment with an oxidizing agent such as, but not limited to, manganese (IV) oxide, barium manganate, 1,1,1-tris(acetyloxy)-1,1-dihydro-1,2-benziodoxol-3-(1H)-one (Dess-Martin periodinane) or catalytic tetrabutylammonium peruthenate (TPAP) combined with a stoichiometric oxidant such as, but not limited to, sodium periodate, or (2,2,6,6-tetramethylpiperidin-1-yl)oxidanyl (TEMPO) combined with a stoichiometric oxidant such as, but not limited to, sodium hypochlorite or manganese (IV) oxide, preferably manganese (IV) oxide, in a solvent such as, but not limited to, dichloromethane, 1,2-dichloroethane or toluene, preferably dichloroethane, at a temperature range of about 0° C. to about 100° C., preferably at room temperature (about 25° C.). After filtration (such as through a pad of Celite™) and solvent evaporation, the product thus obtained was used directly in the next step without purification. An analytically pure sample of Compound IV was obtained through purification by flash column chromatography.

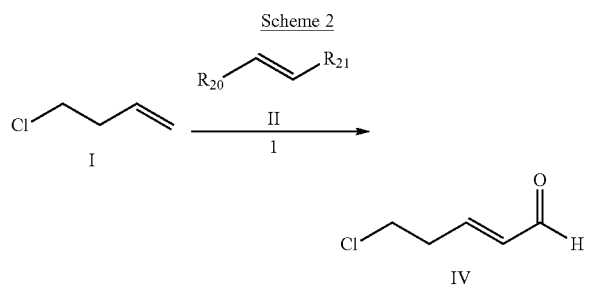

In an alternative and preferable method for preparing Compound IV as depicted in Scheme 2, Compound I was reacted with Compound II (wherein $R_{20}$ is hydrogen or a lower alkyl group and $R_{21}$ is CHO, preferably wherein $R_{20}$ is $CH_3$ (crotonaldehyde)) in the presence of a ruthenium carbene catalyst such as, but not limited to, benzylidene-bis(tricyclohexylphosphine)dichlororuthenium (Grubbs first generation catalyst), (1,3-bis(2,4,6-trimethylphenyl)-2-imidazolidinylidene)dichloro(phenylmethylene)(tricyclohexylphosphine)ruthenium (Grubbs second generation catalyst), (1,3-bis-(2,4,6-trimethylphenyl)-2-imidazolidinylidene)dichloro(o-isopropoxyphenylmethylene)ruthenium (Hoveyda-Grubbs catalyst), or 1,3-bis(2,4,6-trimethylphenyl)-4,5-dihydroimidazol-2-ylidene[2-(i-propoxy)-5-(N,N-dimethylaminosulfonyl)phenyl] methylene ruthenium(II) dichloride (Zhan catalyst 1B), preferably (1,3-bis(2,4,6-trimethylphenyl)-2-imidazolidinylidene)dichloro(phenylmethylene) tricyclohexylphosphine)ruthenium (Grubbs second generation catalyst), in an amount ranging from about 0.1 mol % to about 5 mol %, preferably about 0.5 mol %, in combination with copper(I) iodide, in an amount ranging from about 1 mol % to about 20 mol %, preferably about 6 mol %, at a temperature of about 0° C. to about 100° C., preferably at about 40° C. Upon completion, the reaction mixture was cooled and filtered, and the volatile components which typically include unreacted 4-chloro-1-pentene, unreacted crotonaldehyde and dichloromethane, were removed by distillation under reduced pressure and heating (such as, but not limited to, about 30° C.). After most of the volatile components were removed, the residual product (typically containing small amounts of starting material) was reconstituted (typically in a solvent such as, but not limited to, dichloromethane), and then concentrated again under reduced pressure and heating (such as, but not limited to, about 30° C.) to give (E)-5-chloropent-2-enal as Compound IV, which was used directly in the next step. An analytically pure sample of Compound IV was obtained through purification by flash column chromatography.

The synthesis of Compound III using the ruthenium carbene-catalyzed cross olefin metathesis reactions described herein, represents a significant advantage over traditional, more pedestrian synthetic routes involving the use of organophosphorous reagents such as (dialkoxyphosphoryl)acetates ("Horner-Wadsworth-Emmonds" reagents) or 2-(triphenyl phosphoranylidene)acetaldehyde, which require additional synthetic steps and also may result in waste streams that include aluminum and phosphorus oxides. For example, in the present synthesis, the waste stream includes relatively volatile, unreacted starting materials (such as 4-chloro-2-pentene and crotonaldehyde) and solvent which can be distilled from the product and recycled, catalytic amounts of ruthenium species which can be recovered and recycled, manganese oxides which can be filtered and recycled, and propene gas.

Table 1 below illustrates how conversion rates in the reactions described in Scheme 1 to prepare Compound III (represented by compound 2c) or Compound IV (represented by compound 2a) vary with the choice of Compound II (represented by compound I wherein $R_1$, $R_2$ and $R_3$ have the values shown in each of 1a, 1b and 1c), solvent, temperature, additive, catalyst, catalyst loading, and time.

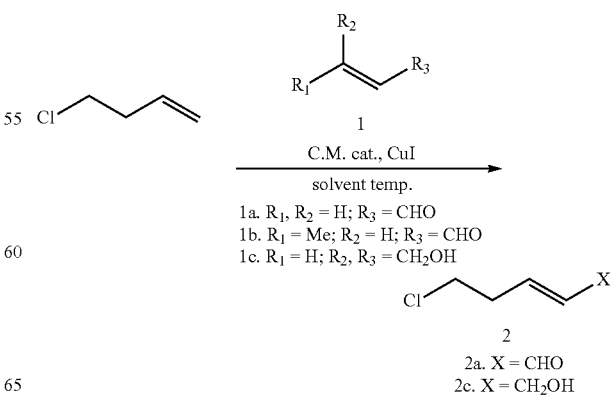

TABLE 1

| Entry | Catalyst | Catalyst Loading (mol %) | CuI (mol %) | 1: (equiv) | Volume (Solvent) | Solvent | Temp. (° C.) | Product | Conver. (%) |
|---|---|---|---|---|---|---|---|---|---|
| 1 | CM-1 | 1 | 3 | 1a; 2 | 20 | DCM | 24 | 2a | 18 |
| 2 | CM-1 | 3 | 3 | 1a; 5 | 10 | DCM | 24 | 2a | 28 |
| 3 | CM-1 | 1 | 3 | 1b; 2 | 20 | DCM | 24 | 2a | 65 |
| 4 | CM-1 | 1 | 3 | 1b; 2 | 30 | DCM | 24 | 2a | 70 |
| 5 | CM-2 | 1 | 3 | 1b; 2 | 30 | DCM | 24 | 2a | 54 |
| 6 | CM-3 | 1 | 3 | 1b; 2 | 30 | DCM | 24 | 2a | 75 |
| 7 | CM-3 | 1 | 6 | 1b; 1.5 | 20 | DCM | 24 | 2a | 66 |
| 8 | CM-3 | 0.5 | 6 | 1b; 1.5 | 20 | DCM | 24 | 2a | 62 |
| 9 | CM-3 | 0.5 | 6 | 1b; 1.5 | 20 | DCM | 40 | 2a | 75 |
| 10 | CM-3 | 0.5 | 6 | 1b; 1.5 | 20 | THF | 40 | 2a | 50 |
| 11 | CM-3 | 0.5 | 6 | 1b; 1.5 | 20 | MTBE | 40 | 2a | 56 |
| 12 | CM-3 | 0.5 | 6 | 1b; 1.5 | 20 | DIE | 40 | 2a | 56 |
| 13 | CM-3 | 0.5 | 6 | 1b; 1.5 | 20 | Toluene | 40 | 2a | 50 |
| 14 | CM-3 | 0.5 | 6 | 1c; 1.5 | 20 | DCM | 40 | 2c | 82 |

CM-1

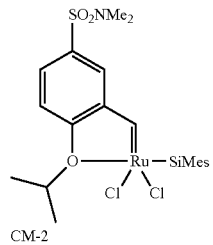

CM-2

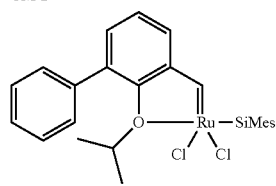

CM-3

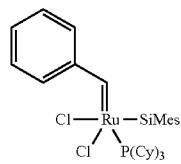

DCM = dichloromethane
THF = tetrahydrofuran
MTBE = methyl tert-butyl ether
DIE = diethyl ether The synthetic reaction described in Scheme 3 involves an asymmetric aldol reaction (Nagao-Aldol reaction) between the aldehyde of Compound IV and the thiazolidine thione of Compound V and was carried out under conditions that are analogous to those described in Ren, Q. et al., *Synlett* 2008, No. 15, 2379-2383.

Scheme 3

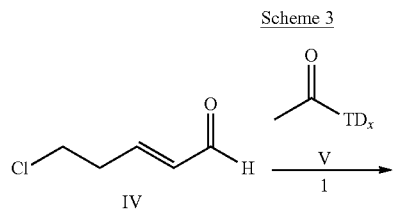

-continued

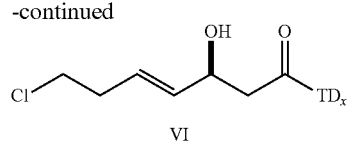

VI

The Nagao-Aldol reaction is particularly useful for preparing stereochemically enriched, β-hydroxy carbonyl compounds which do not contain a substituent other than hydrogen on the carbon alpha to the carbonyl group bearing the chiral auxiliary. In addition, unlike the more traditional "Evans" chiral oxazolidinone chiral auxiliaries, thiazolidine thione auxiliaries serve to activate the carbonyl groups to which they are attached towards nucleophilic addition by amine compounds, in particular primary amines, to give the corresponding amides directly without the need for additional activation. In particular, the acetylated chiral auxiliary V of Scheme 3 (where TDx includes, but is not limited to, (R)-4-isopropylthiazolidine-2-thione, (R)-4-benzylthiazolidine-2-thione, (R)-4-phenylthiazolidine-2-thione or (R)-4-(tert-butyl)thiazolidine-2-thione) was treated with a Lewis acid, a base and the aldehyde of Compound IV to yield Compound VI with a high degree of diastereoselectivity. Compound IV is substituted with a chlorine group in the 5-position which serves a leaving group for the introduction of a thioester group via a nucleophilic displacement reaction involving the salt of a thioic S-acid as described in Schemes XIII and IX. The Nagao-Aldol reaction has previously been used to synthesize intermediates related to Compound VI of Scheme 3, which in turn, were employed in the synthesis of the natural product, Largazole. (Taori, K. et al, *J. Am. Chem. Soc.*, (2008), 130, 1806; Leusch, H. et al., *Nat. Prod. Rep.*, (2012), 29, 449). In the majority of the reported syntheses, a thiol, protected as its triphenylmethyl derivative, was used to eventually deliver the thioester group incorporated in the natural product Largazole and synthetic analogs thereof. (Ying, Y. et al., *J. Am. Chem. Soc.* (2008), 130, 8457; Bowers, A. et al., *J. Am. Chem. Soc.*, (2008), 130, 11221; Xiao, Q. et al., *Journal of Asian Natural Products Research*, (2010), 12:11, 940; Benelkebir, H. et al., *Bioorg. Med. Chem.* (2011), 19, 3650; Bhansali, P. et al., *J. Med. Chem.* (2011), 54, 7453). In addition to masking the thiol as a triphenylmethyl thioether, the use of a trialkylsilyl ether has also been reported. (Ren, Q. et al., *Synlett* (2008), No. 15, 2379-2383). In this case, the protecting group was incompatible with the planned chemistry, which necessitated a protecting group exchange to a disulfide group late in the synthesis. In other reports, the requisite thioester group was introduced in a final step using a cross olefin metathesis reaction. (Nasveschuk, C. G. et al., J., *Org. Lett.* (2008), 10, 3595; Seiser, T. et al, *Angew. Chem. Int. Ed.* (2008), 47, 6483; Souto, J. A. et al., *J. Med Chem.* (2010), 33, 4654). In these published examples, the chemical yield described for this transformation was uniformly low and the catalyst loading was uniformly high. Thus, this particular bond construction was not an attractive option for large scale synthesis.

The present invention demonstrates the use of a chlorine atom as a low molecular weight, "atom-economical" surrogate for a triphenylmethylthio group for preparing depsipeptide derivatives related to Largazole via Compound VI of Scheme 3 which are prepared via a Nagao-Aldol reaction between Compounds IV and V. To prepare the aldol product Compound VI, the N-acylated chiral auxiliary, Compound V, comprising a chiral thiazolidine dione, preferably (R)-1-(4-benzyl-2-thioxothiazolidin-3-yl)ethanone or (R)-1-(4-isopropyl-2-thioxothiazolidin-3-yl)ethanone, is treated with a Lewis acid, such as, but not limited to, a titanium (IV) halide, preferably titanium tetrachloride, in an aprotic solvent such as, but not limited to, dichloromethane, 1,2-dichloroethane or toluene, preferably dichloromethane, at about −78° C. to about 0° C., preferably about −5° C., over a period of about 30 minutes followed by a tertiary amine base such as, but not limited to, triethylamine, (−)-sparteine or diisopropylethyl amine, preferably diisopropylethyl amine, at a temperature of about −78° C. to about 0° C., preferably about −40° C. with stirring for about two hours at which time the resulting solution is cooled to about −90° C. to about −40° C., preferably −78° C. and a solution of the aldehyde of Compound IV, in an aprotic solvent such as, but not limited to, dichloromethane, 1,2-dichloroethane or toluene, preferably dichloromethane, is added.

TABLE 2

| R | X = H; Y = OH (1) | X = OH; Y = H (2) | Isolated Yield | Purification Method |
|---|---|---|---|---|
| VI-A: (CH₃)₂CH— | 9 | 1 | 80 | column chromatography |
| VI-B: PhCH₂— | 5 | 1 | 71 | recrystallization |

Scheme 4 describes the synthesis of Compound X. In Step 1, the secondary hydroxyl group of Compound VI was acylated with a protected amino acid derivative, wherein the protecting group is, for example, tert-butyloxy carbonyl (Boc), (9H-fluoren-9-yl)methyloxy carbonyl (Fmoc), or 2-(trimethylsilyl)ethyloxy carbonyl, preferably tert-butyloxy carbonyl.

Scheme 4

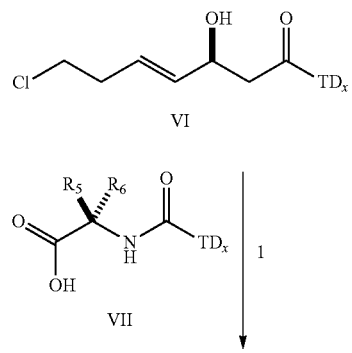

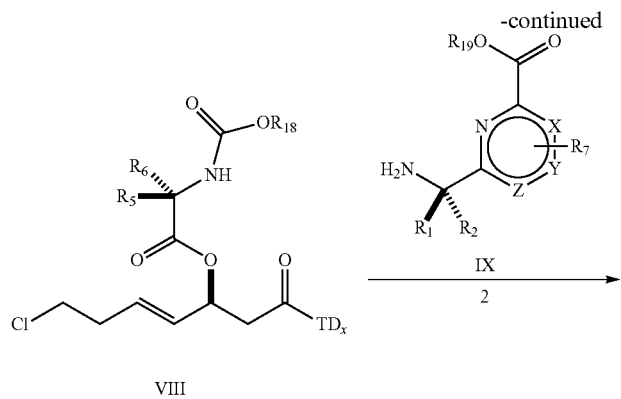

VIII

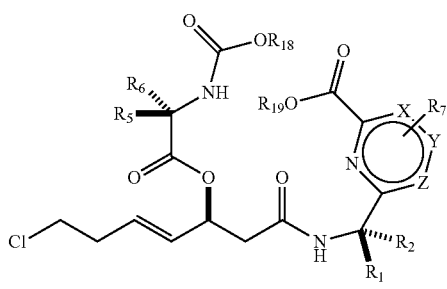

IX

→ 2

X

Step 1 of Scheme 4 describes the ester formation between Compound VI and Compound VII to give Compound VIII where $R_{18}$ of Compound VII includes, but is not limited to, —$CH_2CH_2Si(CH_3)_3$, (9H-fluoren-9-yl)methyl (Fmoc) or tert-butyl (Boc), preferably tert-butyl, and was carried out using an activating agent such as, but not limited to, 1-ethyl-3-(3-dimethylaminopropyl)carbodiimide (EDCI), dicyclohexylcarbodiimide (DCC), diisopropylcarbodiimide (DIC), carbonyldiimidazole (CDI), 2,4,6-trichlorobenzoyl chloride, preferably 1-ethyl-3-(3-dimethylaminopropyl)carbodiimide (EDCI), with an aminopyridine catalyst such as, but not limited to, dimethylaminopyridine or 4-pyrrolidinopyridine, preferably 4-dimethylaminopyridine, in about 5 mol % to about 30 mol %, preferably about 10 mol % in a solvent such as, but not limited to, dichloromethane, 1,2-dichloroethane, acetonitrile, tetrahydrofuran, toluene, heptane, methyl tert-butyl ether, diisopropyl ether, ethyl acetate or isopropyl acetate, dimethyl formamide, dimethyl acetamide or N-methyl pyrroldinone, preferably dichloromethane, at a temperature of about 0° C. to about 40° C., preferably at room temperature (about 25° C.).

Step 2 of Scheme 4 is an amide-forming reaction wherein the chiral thiazolidine thione group of Compound VIII serves to activate the carbonyl to which it is attached towards nucleophilic displacement by a primary amine as previously discussed. In this reaction, Compound IX is a 5- or 6-membered heterocyclic moiety that contains at least one nitrogen in the heterocyclic ring, with a carboxylate group, suitably protected as an ester, attached to the same carbon as the nitrogen atom, and a substituted or unsubstituted methylamino group attached to the other carbon atom to which the nitrogen is attached. Thus, each group, ester and substituted or unsubstituted methyl amino, are situated ortho to a nitrogen atom in the heterocyclic ring, and meta to each other. The 5- or 6-membered heterocyclic moiety of Compound IX includes, but is not limited to, pyridine, pyrimidine, pyrazine, triazine, oxazole, thiazole, oxadiazole, or thiadiazole. In an exemplary embodiment, this moiety is thiazole or tert-butyl 2-(aminomethyl)thiazole-4-carboxylate. The reaction was typically performed by dissolving Compound VIII of Scheme 4 in an aprotic solvent such as, but not limited to, dichloromethane, 1,2-dichloroethane, acetonitrile, tetrahydrofuran, toluene, heptane, methyl tenbutyl ether, diisopropyl ether, ethyl acetate or isopropyl acetate, dimethyl formamide, dimethyl acetamide or N-methyl pyrroldinone, preferably dichloromethane, followed by adding Compound VI and stirring for about 1 hour to about 48 hours, preferably about 24 hours, at a temperature of about 0° C. to about 40° C., preferably at room temperature (about 25° C.).

Scheme 5 describes an alternative and more preferable synthesis of Compound X. In Step 1 of Scheme 5, the Nagao-Aldol product of Compound VI, is dissolved in an aprotic Scheme 5

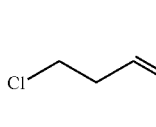

VI

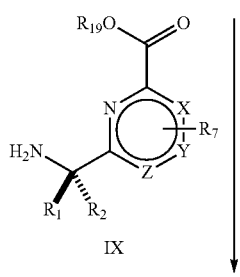

IX

1

↓

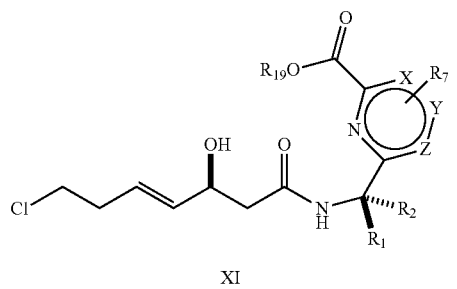 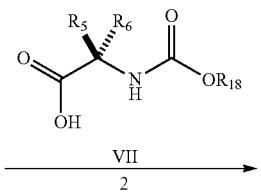 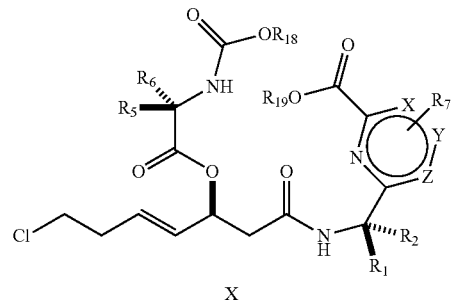

XI → X solvent such as, but not limited to, dichloromethane, 1,2-dichloroethane, acetonitrile, tetrahydrofuran, toluene, heptane, methyl tert-butyl ether, diisopropyl ether, ethyl acetate, isopropyl acetate, dimethyl formamide, dimethyl acetamide or N-methyl pyrroldinone, preferably dichloromethane, was treated with Compound IX (where $R_{19}$ is, for example, tert-butyl or $CH_2CH_2Si(CH_3)_3$, preferably tert-butyl) and stirred for about 1 hour to about 48 hours, preferably about 24 hours, at a temperature of about 0° C. to about 40° C., preferably at room temperature (about 25° C.). Water was added, the organic layer was separated, and the aqueous layer was extracted once with dichloromethane. The organic layers were combined, washed with brine and concentrated under vacuum. Trituration with ethyl acetate provided Compound XI in 70-80% yield. Purification of the mother liquor by column chromatography provided additional Compound XI along with the recovered chiral auxiliary which can be reused to synthesize Compound V as shown in Table 2.

In Step 2 of Scheme 5, the secondary hydroxyl group of Compound XI was acylated with the protected amino acid derivative of Compound VII, wherein the protecting group is, for example, tert-butyloxy carbonyl (Boc), (9H-fluoren-9-yl)methyloxy carbonyl (Fmoc) or 2-(trimethylsilyl)ethyl-oxy carbonyl, preferably tert-butyloxy carbonyl, to provide Compound X. The reaction was carried out using an activating agent, such as, but not limited to, dicyclohexylcarbodiimide (DCC), diisopropylcarbodiimide (DIC) or 1-ethyl-3-(3-dimethylaminopropyl)carbodiimide (EDCI), preferably 1-ethyl-3-(3-dimethylaminopropyl)carbodiimide (EDCI), in a solvent such as, but not limited to, dichloromethane, 1,2-dichloroethane, acetonitrile, tetrahydrofuran, toluene, heptane, methyl tert-butyl ether, diisopropyl ether, ethyl acetate or isopropyl acetate, dimethyl formamide, dimethyl acetamide or N-methyl pyrrolidinone, preferably dichloromethane, with an aminopyridine catalyst such as, but not limited to, dimethylaminopyridine or 4-pyrrolidinopyridine, preferably 4-dimethylaminopyridine, in about 5 mol % to about 30 mol %, preferably about 10 mol % at a temperature of about 0° C. to about 40° C., preferably at room temperature (about 25° C.). Water was added to the reaction mixture and the organic layer was separated and washed once with water. The organic layer was dried and concentrated to give Compound X which was used without further purification.

Scheme 6 describes the preparation of the heterocyclic amino acid derivative of Compound XV which exemplifies Compound IX of Schemes 4 and 5. Compound XII and Compound XIII were combined in a solvent such as, but not limited to, 1,2-dimethoxyethane (DME), tetrahydrofuran (THF) or 1,4-dioxane, preferably 1,2-dimethoxyethane (DME), and a base was added such as, but not limited to, sodium hydrogen carbonate or potassium hydrogen carbonate, preferably potassium hydrogen carbonate, at a temperature of about −40° C. to about 25° C., preferably about −10° C. After stirring for about 10 min to about 24 hours, Scheme 6

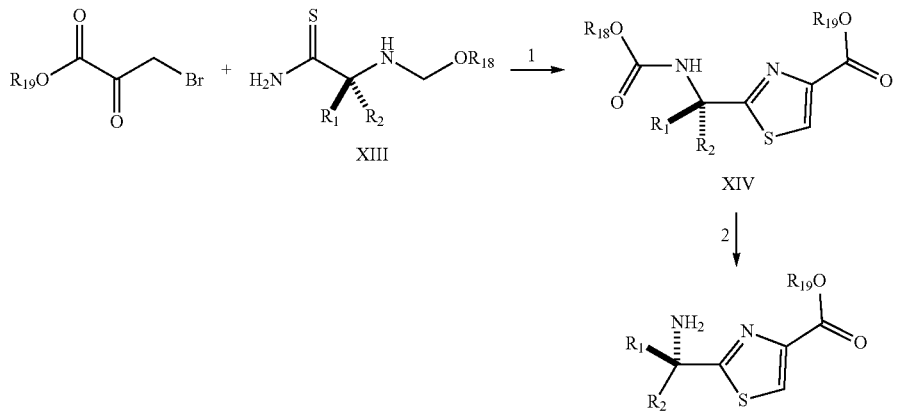

preferably about 1 hour, a solution of trifluoroacetic anhydride and a base such as, but not limited to, pyridine, 2-methylpyridine, 2,6-dimethyl pyridine, 2,3,5-trimethylpyridine or 2,4,6-trimethylpyridine, preferably 2,6-dimethylpyridine, in a solvent such as, but not limited to, 1,2-dimethoxyethane (DME), tetrahydrofuran (THF) or 1,4-dioxane, preferably 1,2-dimethoxyethane, was added at a temperature of about −40° C. to about 25° C., preferably about -20° C. After stirring for about 10 min to about 24 hours, preferably about 2 hours, the mixture was poured into water and subsequent extractive workup provided Compound XIV as a solid.

In an alternative and preferable method for preparing Compound XV of Scheme 6 Compound XII of Scheme 6 was combined with Compound XIII of Scheme 6 in a solvent such as, but not limited to, methanol, ethanol, isopropanol, sec-butanol, dichloromethane, 1,2-dichloroethane, acetonitrile, tetrahydrofuran, toluene, heptane, methyl tert-butyl ether, diisopropyl ether, 1,2-dimethoxy ethane, 1,4-dioxane, ethyl acetate, isopropyl acetate, dimethyl formamide, dimethyl acetamide or N-methyl pyrroldinone, preferably isopropanol, and stirred at a temperature of about 0° C. to about 100° C., preferably about 25° C., in the absence of, or in the presence of a base such as, but not limited to, aqueous sodium hydroxide, aqueous potassium hydroxide, aqueous lithium hydroxide, or calcium carbonate, preferably aqueous sodium hydroxide, for a period of about 1 hour to about 72 hours, preferably about 24 hours. The reaction was diluted with water and Compound XIV was obtained after subsequent extractive workup.

Scheme 7a describes the selective removal of the carbamate protecting group bearing $R_{18}$ within Compound XVI, in the presence of the ester group bearing $R_{19}$, to provide Compound XVII.

Thus, the carbamate protecting group bearing $R_{18}$ and the ester group bearing $R_{19}$ within Compound XVI are orthogonal protecting groups with respect to their structure or reactivity. $R_{18}$ of Compound XVI includes, but is not limited to, —$CH_2CH_2Si(CH_3)_3$. (9H-fluoren-9-yl)methyl (Fmoc) or tert-butyl (Boc). $R^{19}$ of Compound XVI includes, but is not limited to, —$CH_2CH_2Si(CH_3)_3$ or tert-butyl (Boc). When $R_{18}$ of Compound XVI is —$CH_2CH_2Si(CH_3)_2$, Step 1 of Scheme 7a was carried out by treating Compound XVI with a fluoride source such as, but not limited to, potassium fluoride, cesium fluoride, tetrabutylammonium fluoride or lithium tetrafluoroborate, preferably tetrabutylammonium fluoride in a solvent such as, but not limited to, tetrahydrofuran, acetonitrile, dimethyl formamide, N-methylpyrrolidone, N,N-dimethyl acetamide or dimethyl sulfoxide, preferably tetrahydrofuran, at a temperature of about 0° C. to about 65° C., preferably at room temperature (about 25° C.).

When $R_{18}$ of Compound XVI is (9H-fluoren-9-yl)methyl (Fmoc), Step 1 of Scheme 7a was carried out by treating Compound XVI with an amine base such as, but not limited to, morpholine, piperidine, piperazine, 1,4-bis-(3-aminopropyl)piperazine, dicyclohexylamine, diisopropylethyl amine, 4-dimethylaminopyridine, 1,8-Diazabicyclo[5.4.0]undec-7-ene, pyrrolidine, cyclohexylamine, ethanolamine, diethylamine, triethylamine, ammonia, tributylamine or triethylenediamine, preferably piperidine, in a solvent such as, but not limited to, dichloromethane, 1,2-dichloroethane, dimethyl formamide, n-methylpyrolidinone, or N,N-dimethylacetamide, preferably dichloromethane, at a temperature of about −20° C. to about 40° C., preferably at room temperature (about 25° C.).

Scheme 7a

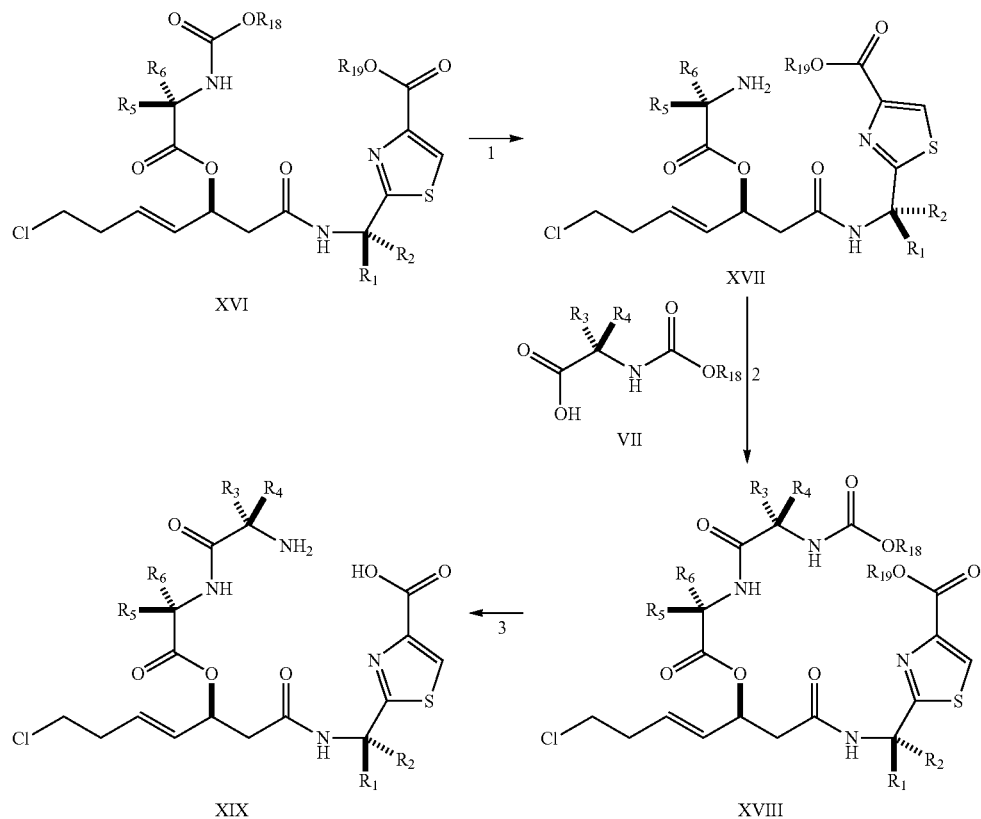

When $R_{18}$ of Compound XVI is tert-butyl (Boc), Step 1 of Scheme 7a was carried out by treating Compound XVI with an acid such as, for example, trifluoroacetic acid or HCl, dissolved in an organic solvent such as, for example, dichloromethane, toluene, ethyl acetate, THF, DME, MTBE, or dioxane, at a temperature of about 0° C. to about 40° C., preferably at room temperature (about 25° C.). Preferably, $R_{18}$ of Compound XVI is tert-butyl and Step 1 is carried out preferably with HCl in dioxane, more preferably at room temperature (about 25° C.). The reaction mixture was poured into a cooled, saturated solution of sodium bicarbonate at about pH 8-9, and the resulting mixture was twice extracted with ethyl acetate, once with brine, dried, and concentrated to dryness to provide Compound XVII in about 95% yield, and which was used directly in the next step without further purification.

In Step 2 of Scheme 7a, Compound XVII was converted to Compound XVIII by treatment with Compound VII and an activating agent such as, but not limited to, dicyclohexylcarbodiimide (DCC), diisopropylcarbodiimide (DIC) or 1-ethyl-3-(3-dimethylaminopropyl)carbodiimide (EDCI), preferably 1-ethyl-3-(3-dimethylaminopropyl)carbodiimide (EDCI) by itself or in the presence of an additive such as, but not limited to, hydroxybenztriazole (HOBt) or 1-hydroxy, 7-azabenztriazolein, preferably hydroxybenztriazole (HOBt), in a solvent such as, but not limited to, dichloromethane, 1,2-dichloroethane, acetonitrile, tetrahydrofuran, toluene, heptane, methyl tert-butyl ether, diisopropyl ether, ethyl acetate or isopropyl acetate, dimethyl formamide, dimethyl acetamide or N-methyl pyrroldinone, preferably dichloromethane, at a temperature of about −20° C. to about 60° C., preferably at room temperature (about 25° C.).

In Step 3 of Scheme 7a, Compound XIX was produced by simultaneous hydrolysis of the carbamate and ester groups bearing $R_{18}$ and $R_{19}$ respectively, within Compound XVIII. Thus, for example when $R_{18}$ and $R_{19}$ are both —$CH_2CH_2Si(CH_3)_3$, Step 3 was carried out by treating Compound XVIII, with, for example, potassium fluoride, cesium fluoride, tetrabutylammonium fluoride, lithium tetrafluoroborate, or trifluoroacetic acid, preferably tetrabutylammonium fluoride, in a solvent such as, but not limited to, tetrahydrofuran, acetonitrile, dimethyl formamide, N-methylpyrrolidinone, N,N-dimethyl acetamide or dimethyl sulfoxide, preferably tetrahydrofuran, at a temperature of about 0° C. to about 40° C., preferably at room temperature (about 25° C.).

Alternatively and preferably, when $R_{18}$ and $R_{19}$ are both tert-butyl, Step 3 of Scheme 7a was carried out by treating Compound XVIII with an acid such as, but not limited to, trifluoroacetic acid or HCl, preferably trifluoroacetic acid, in a solvent such as, but not limited to, dichloromethane, 1,2-dichloroethane, or toluene, preferably dichloromethane, at a temperature of about 0° C. to about 40° C., preferably at room temperature (about 25° C.).

Scheme 7b des the concomitant removal of the carbamate protecting group bearing $R_{18}$ within Compound XVI, and the ester group bearing $R_{19}$, to provide Compound XVII-A. Preferably, when $R_{18}$ and $R_{19}$ are both tert-butyl, Step 1 of Scheme 7b is carried out by treating Compound XVI with an acid such as, but not limited to, trifluoroacetic acid or HCl, preferably trifluoroacetic acid, in a solvent such as, but not limited to, dichloromethane, 1,2-dichloroethane, or toluene, preferably dichloromethane, at a temperature of about 0° C. to about 40° C., preferably at room temperature (about 25° C.).

Scheme 7b

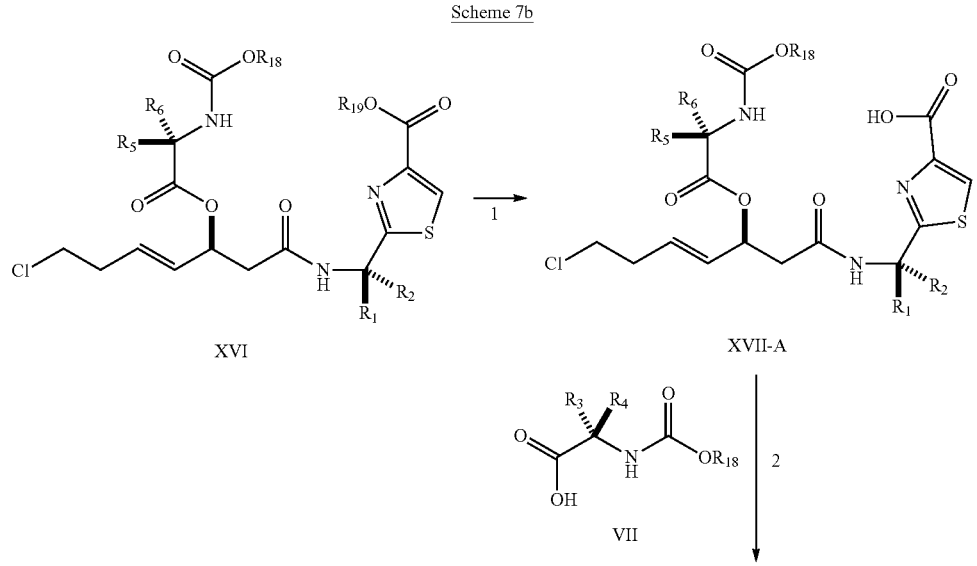

-continued

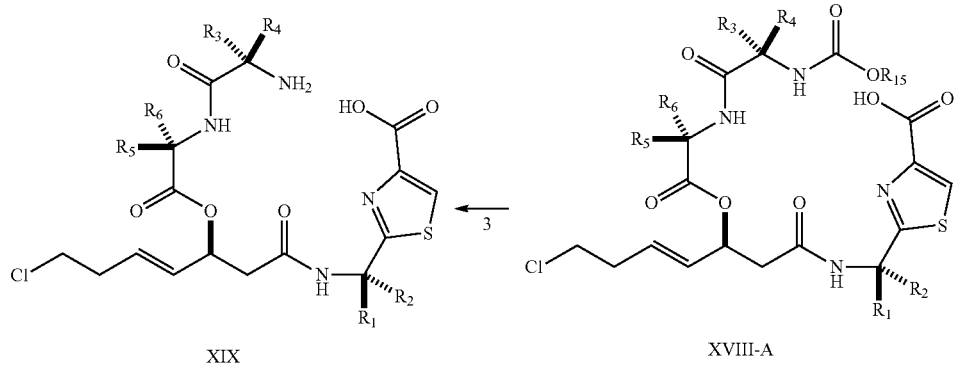

XIX

XVIII-A

In Step 2 of Scheme 7b. Compound XVII-A was converted to Compound XVIII-A by treatment with Compound VII and an activating agent such as, but not limited to, dicyclohexylcarbodiimide (DCC), diisopropylcarbodiimide (DIC) or 1-ethyl-3-(3-dimethylaminopropyl)carbodiimide (EDCI), preferably 1-ethyl-3-(3-dimethylaminopropyl)carbodiimide (EDCI) by itself or in the presence of an additive such as, but not limited to, hydroxybenztriazole (HOBt) or 1-hydroxy, 7-azabenztriazolein, preferably hydroxybenztriazole ($HOB_t$), in a solvent such as, but not limited to, dichloromethane, 1,2-dichloroethane, acetonitrile, tetrahydrofuran, toluene, heptane, methyl tert-butyl ether, diisopropyl ether, ethyl acetate or isopropyl acetate, dimethyl formamide, dimethyl acetamide or N-methyl pyrroldinone, preferably dichloromethane, at a temperature of about −20° C. to about 60° C., preferably at room temperature (about 25° C.).

In Step 3 of Scheme 7b, Compound XIX was produced by hydrolysis of the carbamate and ester group bearing $R_{18}$ within Compound XVIII-A. Thus, for example when $R_{18}$ is tert-butyl, Step 3 of Scheme 7b was carried out by treating Compound XVIII-A with an acid such as, but not limited to, trifluoroacetic acid or HCl, preferably trifluoroacetic acid, in a solvent such as, but not limited to, dichloromethane, 1,2-dichloroethane, or toluene, preferably dichloromethane, at a temperature of about 0° C. to about 40° C., preferably at room temperature (about 25° C.).

Step 1 of Scheme 8 is a macrolactamization reaction whereby the amino group of Compound XIX is acylated in an intramolecular fashion by the carboxylic acid group in Scheme 8

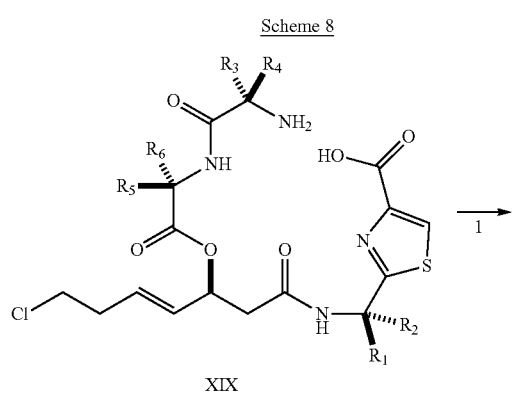

XIX

-continued

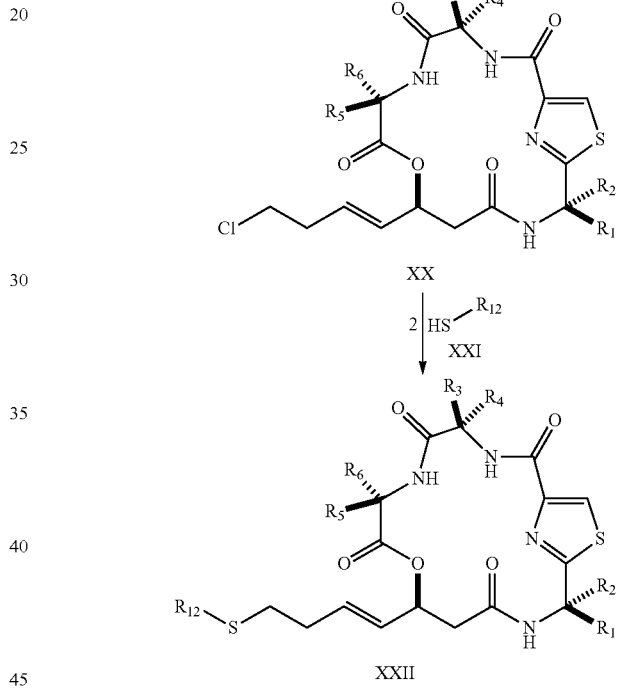

XX

XXII

Compound XIX to afford Compound XX. Step 1 was carried out by treatment of Compound XIX with an activating agent such as, but not limited to, N-[(dimethylamino)-1H-1,2,3-triazolo-[4,5-b]pyridin-1-ylmethylene]-N-methylmethanaminium hexafluorophosphate N-oxide(HATU), (O-(7-azabenztriazol-1-yl)-1,1,3,3-bis(tetramethylene)uranium hexafluorophosphate)(HBTU), N,N,N',N'-tetramethyl-O-(1H-benzotriazol-1-yl)uronium hexafluorophosphate, O-(benzotriazol-1-yl)-N,N,N',N'-tetramethyluronium hexafluorophosphate, DCC, DIC, EDCI, BDDC, BOP, PyBOP, BOMP, AOP, PyAOP, PyDOP, PyNOP, PyFOP, PyNFOP, NOP, NSBt, N-NSBt, N-HBTU, V-HATU or (HAPyU), preferably N-[(dimethylamino)-1H-1,2,3-triazolo-[4,5-b]pyridin-1-ylmethylene]-N-methylmethanaminium hexafluorophosphate N-oxide (HATU), by itself or in or in the presence of an additive such as, but not limited to, (HOSuc), (HODhbt), (HOt), (HOCt), (Oxama), ($6\text{-}CF_3\text{-}$ HOBt), ($6\text{-}NO_2\text{-}HOBt$), hydroxy-1,2,3-triazole, hydroxybenztriazole (HOBt) or 1-hydroxy-7-azabenztriazolein (HOAt), preferably hydroxybenztriazole (HOBt), in a solvent such as, but not limited to, dichloromethane, 1,2-dichloroethane, acetonitrile, tetrahydrofuran, toluene, heptane, methyl tert-butyl ether, diisopropyl ether, ethyl acetate or isopropyl acetate, dimethyl formamide, dimethyl acetamide or N-methyl pyrroldinone, preferably a combination of dichloromethane and dimethylformamide in a ratio of about 20:1 to about 1:1, preferably about 10:1, at a concentration of about 5 volumes to about 50 volumes with respect to Compound XIX, preferably at 10 volumes, at a temperature of about 0° C. to about 40° C., preferably at room temperature (about 25° C.).

In Step 2 of Scheme 8, Compound XX was converted to Compound XXII. The reaction was carried out by treating Compound XX with a thioate nucleophile prepared from the treatment of Compound XXI with a base such as, but not limited to, potassium hydroxide, sodium hydroxide, lithium hydroxide, cesium carbonate, potassium carbonate, sodium carbonate, lithium carbonate, potassium hydrogen carbonate, sodium hydrogen carbonate, sodium methoxide, potassium tert-butoxide, triethyl amine, N,N-diisopropylethylamine or 1,8-diazabicyclo[5.4.0]undec-7-ene, preferably potassium carbonate, in a solvent such as, but not limited to, acetone, acetonitrile, tetrahydrofuran, diisopropyl ether, methyl tert-butyl ether, 1,2-dimethoxyethane, 1,4-dioxane, toluene, dichloromethane, 1,2-dichloroethane, ethyl acetate, isopropyl acetate, methanol, ethanol, water, dimethyl formamide, N-methyl pyrrolidinone, N,N-dimethyl acetamide or dimethyl sulfoxide, preferably acetonitrile, at a temperature of about −10° C. to about 100° C., preferably about 60° C. The thioate intermediate was formed either by itself and then added to the reaction mixture, or formed in situ, preferably in situ, in the absence of, or in the presence of sodium iodide or potassium iodide, preferably in the presence of potassium iodide, in an amount of about 5 mol % to about 300 mol %, preferably about 100 mol %.

In Step 1 of Scheme 9, Compound XX is converted to Compound XXIV. The

Scheme 9

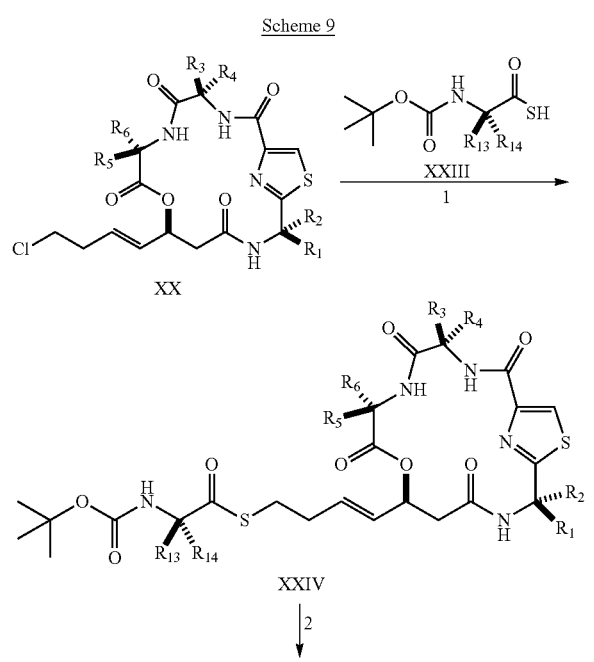

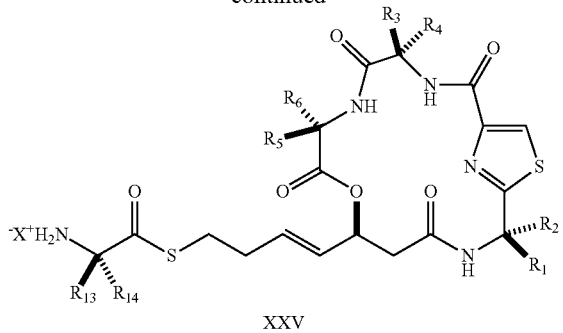

reaction was carried out by treating Compound XX with a thioate nucleophile prepared from the treatment of Compound XXIII with a base such as, but not limited to, potassium hydroxide, sodium hydroxide, lithium hydroxide, cesium carbonate, potassium carbonate, sodium carbonate, lithium carbonate, potassium hydrogen carbonate, sodium hydrogen carbonate, sodium methoxide, potassium tert-butoxide, triethyl amine, N,N-diisopropylethylamine or 1,8-diazabicyclo[5.4.0]undec-7-ene, preferably potassium carbonate, in a solvent such as, but not limited to, acetone, acetonitrile, tetrahydrofuran, diisopropyl ether, methyl tert-butyl ether, 1,2-dimethoxyethane, 1,4-dioxane, toluene, dichloromethane, 1,2-dichloroethane, ethyl acetate, isopropyl acetate, methanol, ethanol, water, dimethyl formamide, N-methyl pyrrolidinone, N,N,-dimethyl acetamide or dimethyl sulfoxide, preferably acetonitrile, at a temperature of about −10° C. to about 100° C., preferably about 60° C. The thioate intermediate was formed either by itself and then added to the reaction mixture or formed in situ, preferably in situ, in the absence of, or in the presence of sodium iodide or potassium iodide, preferably in the presence of potassium iodide, in an amount of about 5 mol % to about 300 mol %, preferably about 100 mol %.

In Step 2 of Scheme 9, Compound XXIV was converted to Compound XXV. The reaction was carried out by treating Compound XXIV with an acid.

In addition to having utility in preparation of the therapeutic agents of Formula (1), Compound VIII of Scheme 10, wherein $R^{18}$ is described above, is useful in the preparation of Largazole and Largazole analogs described in, for example, U.S. Published Application No. 20100029731 to Williams et al.

As shown in step 1 of Scheme 10. Compound VIII was treated with Compound XXVI in a manner analogous to conditions described in Xie et al., *Journal of Asian Nat. Prod. Res.* (2010), 12, 940-949 to provide Compound XXVII.

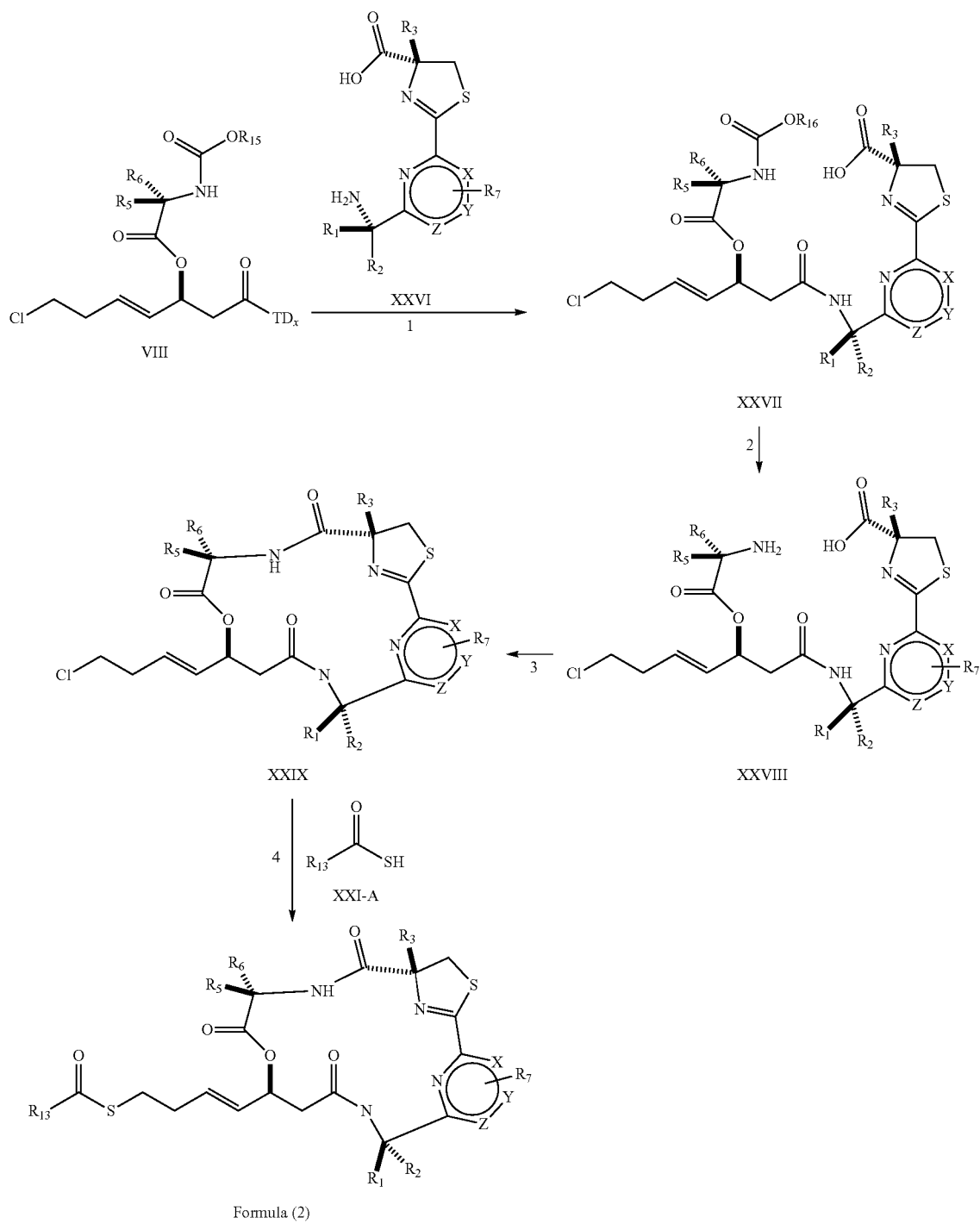

Formula (2)

In Step 2 of Scheme 10, Compound XXVII was converted to the corresponding amino acid via Boc group deprotection to give Compound XXVIII.

In Step 3 of Scheme 10, Compound XXVIII was converted to Compound XXIX via a macrolactamization reaction by treatment with an activating agent such as, but not limited to, N-[(dimethylamino)-1H-1,2,3-triazolo-[4,5-b]pyridin-1-ylmethylene]-N-methylmethanaminium hexafluorophosphate N-oxide (HATU), (O-(7-azabenztriazol-1-yl)-1,1,3,3-bis(tetramethylene)uranium hexafluorophosphate)(HBTU). N,N,N',N'-tetramethyl-O-(1H-benzotriazol-1-yl)uronium hexafluorophosphate, O-(benzotriazol-1-yl)-N,N,N',N'-tetramethyluronium hexafluorophosphate, DCC, DIC, EDCI, BDDC, BOP, PyBOP, BOMP, AOP, PyAOP, PyDOP, PyNOP, PyFOP, PyNFOP, NOP, NSBt, N-NSBt, N-HBTU, N-HATU or (HAPyU), preferably N-[(dimethylamino)-1H-1,2,3-triazolo-[4,5-b]pyridin-1-yl-methylene]-N-methylmethanaminium hexafluorophosphate. N-oxide (HATU), by itself or in or in the presence of an additive such as, but not limited to, (HOSuc), (HODhbt), (HOt), (HOCt), (Oxama), (6-CF$_3$-HOBt), (6-NO$_2$-HOBt), hydroxy-1,2,3-triazole, hydroxybenztriazole (HOBt) or 1-hydroxy-7-azabenztriazolein (HOAt), preferably hydroxybenztriazole (HOBt), in a solvent such as, but not limited to, dichloromethane, 1,2-dichloroethane, acetonitrile, tetrahydrofuran, toluene, heptane, methyl tert-butyl ether, diisopropyl ether, ethyl acetate or isopropyl acetate, dimethyl formamide, dimethyl acetamide or N-methyl pyrroldinone, preferably a combination of dichloromethane and dimethylformamide in a ratio of about 20:1 to about 1:1, preferably about 10:1, at a concentration of about 5 volumes to about 50 volumes with respect to Compound XIX, preferably at 10 volumes, at a temperature of about 0° C. to about 40° C., preferably at room temperature (about 25° C.).

In step 4 of Scheme 10, Compound XXIX was converted to a compound of Formula (2). The reaction was carried out by treating Compound XXIX with a thioate nucleophile prepared from the treatment of Compound XXI-A with a base such as, but not limited to, potassium hydroxide, sodium hydroxide, lithium hydroxide, cesium carbonate, potassium carbonate, sodium carbonate, lithium carbonate, potassium hydrogen carbonate, sodium hydrogen carbonate, sodium methoxide, potassium tert-butoxide, triethyl amine, N,N-diisopropylethylamine or 1,8-diazabicyclo[5.4.0]undec-7-ene, preferably potassium carbonate, in a solvent such as, but not limited to, acetone, acetonitrile, tetrahydrofuran, diisopropyl ether, methyl tert-butyl ether, 1,2-dimethoxyethane, 1,4-dioxane, toluene, dichloromethane, 1,2-dichloroethane, ethyl acetate, isopropyl acetate, methanol, ethanol, water, dimethyl formamide, N-methyl pyrrolidinone, N,N,-dimethyl acetamide or dimethyl sulfoxide, preferably acetonitrile, at a temperature of about −10° C. to about 100° C., preferably about 60° C. The thioate intermediate was formed either by itself and then added to the reaction mixture, or formed in situ, preferably in situ, in the absence of, or in the presence of sodium iodide or potassium iodide, preferably in the presence of potassium iodide, in an amount of about 5 mol % to about 300 mol %, preferably about 100 mol %.

EXAMPLES

Example 1

Preparation of S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) octanethioate (Compound XXII) from ((7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-dien-2,5,8,12-tetraone) (Compound XX).

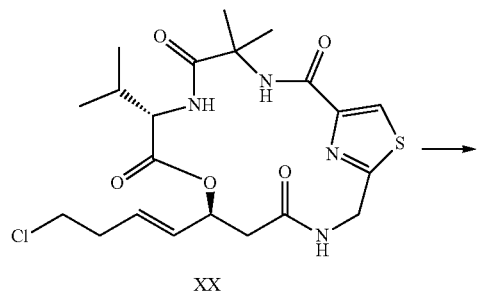

XX

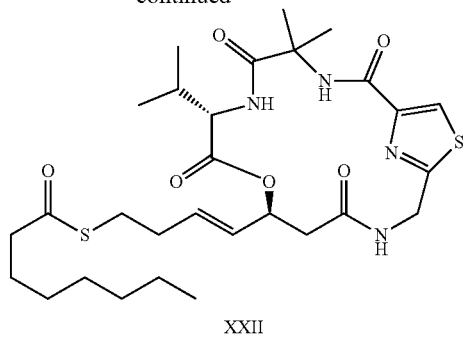

XXII ((7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone)(1.0 g, 2.07 mmol), octanethioic S-acid (0.66 g, 4.13 mmol), potassium carbonate (0.57 g, 4.13 mmol) and potassium iodide (0.067 g, 0.41 mmol) were dissolved in acetonitrile (20 mL) at room temperature. The mixture was stirred at room temperature under nitrogen for 16 hours. The mixture was filtered, concentrated and purified by flash chromatography on silica gel (petroleum ether/ethyl acetate/methanol 20/20/1) to give 1.13 g, (90%) of S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) octanethioate as a tan solid. $^1$H NMR: (CDCl$_3$, 400 MHz): δ 8.02 (a, 1H), 7.65 (s, 1H), 6.63 (d, J=9.6 Hz, 1H), 6.46 (m, 1H), 5.79-5.73 (m, 2H), 5.60 (m, 1H), 5.15 (dd, J=17.6, 8.2 Hz, 1H), 4.63 (m, 1H), 4.36 (dd, J=17.2, 4.0 Hz, 1H), 2.86 (t, J=7.2 Hz, 2H), 2.71 (m, 2H), 2.51 (t, J=7.6 Hz, 2H), 2.30 (m, 3H), 1.89 (s, 3H), 1.61 (s, 3H), 1.28 (bs, 10H), 0.88 (m, 6H), 0.69 (d, J=6.8 Hz, 3H).

Example 2

Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate (Compound XXIV) from (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone)(Compound XX) and (S)-2-((tert-butoxycarbonyl)amino)-3-methylbutanethioic S-acid (Compound XXIII).

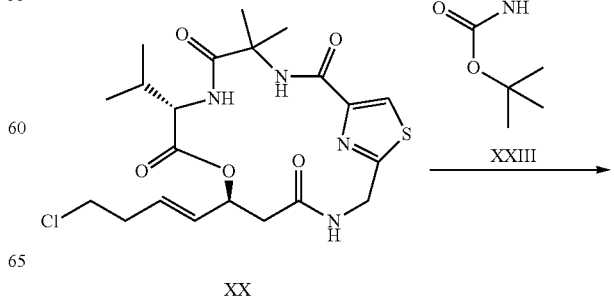

XX  XXIII

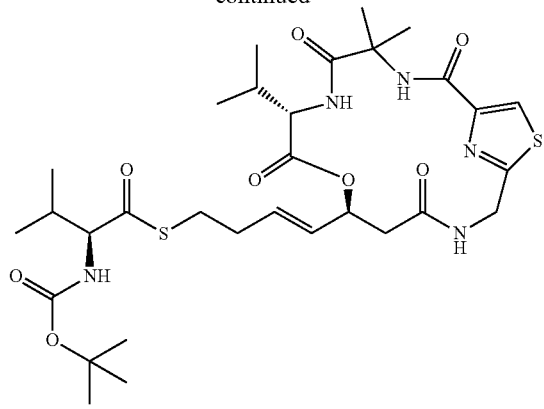

XXIV

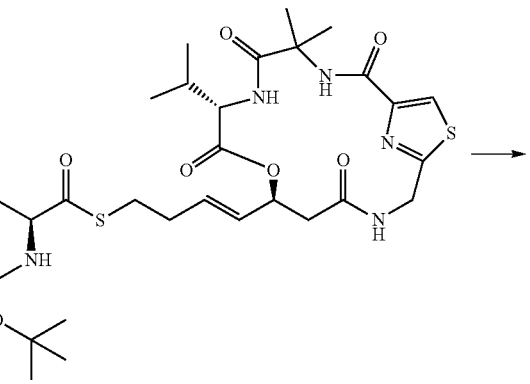

XXIV

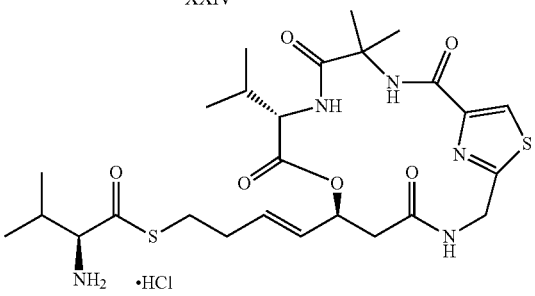

XXV-A (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone)(15 g, 0.031 mmol), (S)-2-((tert-butoxycarbonyl)amino)-3-methylbutanethioic S-acid (Boc-(D)Val-SH) (12.5 g, 0.054 mmol), potassium carbonate (11.2 g, 0.081), and potassium iodide (0.50 g, 0.003 mmol) were dissolved in 10 mL of acetonitrile and the resulting mixture was warmed to 60-65° C. and stirred under nitrogen for 18 hrs. The reaction mixture was cooled to room temperature, water (50 mL) was added, and the resulting mixture was extracted with ethyl acetate (50 mL) twice. The combined organic layers were washed with 40 mL of water, dried with anhydrous sodium sulfate and concentrated and purified by flash chromatography on silica gel (petroleum ether/ethyl acetate 80/20) to give 16.90 g (80%) of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate as a foamy solid. $^1$H NMR: (CDCl$_3$, 400 MHz): δ 8.02 (s, 1H), 7.64 (s, 1H), 6.62 (bs, 1H), 6.50 (d, J=9.6 Hz, 1H), 5.70-5.69 (m, 3H), 5.18 (dd, J=17.6, 8.0 Hz, 1H), 5.06 (d, J=9.6 Hz, 1H), 4.63 (m, 1H), 4.38 (dd, J=9.6 Hz, 6 Hz, 1H), 4.24 (dd, J=9.2, 4.8 Hz, 1H), 2.92 (t, J=7.0 Hz, 2H), 2.70-2.65 (m, 2H), 2.31 (m, 4H), 2.30 (m, 3H), 1.90 (s, 3H), 1.61 (s, 3H), 1.45 (s, 9H), 0.99 (d, 0.1=6.4 Hz, 3H), 0.89 (d, J=7.2 Hz, 3H), 0.86 (d, J=6.8 Hz, 3H), 0.69 (d, J=7.2 Hz, 3H).

((S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)$_2$-((tert-butoxycarbonyl)amino)-3-methylbutanethioate)(8.0 g, 11.7 mmol) was dissolved in 160 mL dichloromethane and trifluoroacteic acid (24 ml) was added at 10° C. under nitrogen. After the addition, the mixture was stirred at room temperature for 5 hours at which time it was concentrated to dryness. The residue was dissolved in ethyl acetate (50 ml), and a solution of HCl in ethyl acetate (10.0 ml, 4.0M) was added slowly dropwise, and the resulting mixture stirred for 10 minutes after the addition was complete. Petroleum ether (50 ml) was then added and the precipitated solid was collected by filtration and dried under vacuum to afford 6.88 g (95%) of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate hydrochloride as a white solid. $^1$H NMR: (DMSO-d$_6$, 400 MHz): δ 8.55 (bs, 4H), 8.16 (s, 1H), 7.90 (m, 2H), 5.63 (m, 3H), 4.97 (dd, J=17.6, 8.2 Hz, 1H), 4.34-4.30 (m, 2H), 4.08 (m, 1H), 3.04 (m, 1H), 2.96 (m, 1H), 2.76 (m, 114), 2.20-2.08 (m, 4H), 1.71 (s, 3H), 1.46 (s, 3H), 0.99 (d, J=6.4 Hz, 3H), 0.96 (d, J=6.4 Hz, 3H), 0.78 (d, J=6.8 Hz, 3H), 0.57 (d, J=6.8 Hz, 3H).

Example 3a

Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate hydrochloride (Compound XXV-A) from ((S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)$_2$-((tert-butoxycarbonyl)amino)-3-methylbutanethioate)(Compound XXIV).

Example 3b

Preparation of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate (Compound XXV-B) from ((S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-((tert-butoxycarbonyl)amino)-3-methylbutanethioate)(Compound XXIV).

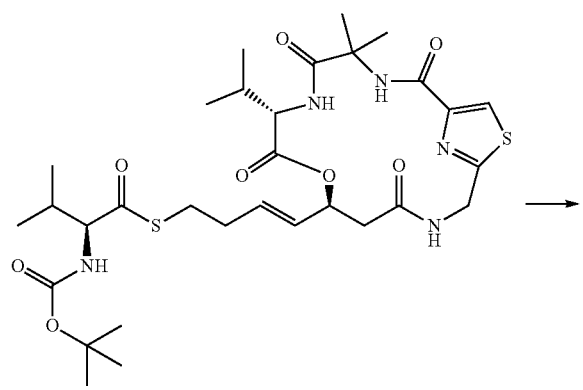

XXIV

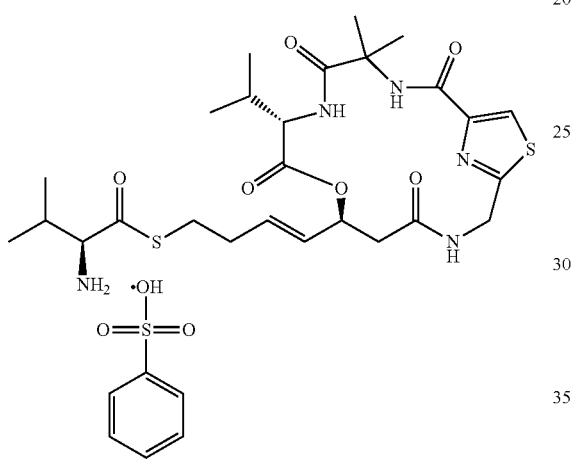

XXV-B

To a solution of ((S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl)$_2$-((tert-butoxycarbonyl)amino)-3-methylbutanethioate)(3.0 g, 4.41 mmol) in 50 mL acetonitrile was added benzenesulfonic acid (2.70 g, 17.10 mmol) at room temperature and the resulting mixture was stirred for 5 hours at which time it was concentrated to dryness. The residue was suspended in heptane (100 ml), and stirred for 30 minutes at which time the heptane was removed by decanting. The oily residue was then treated with THF (5 ml) and stirred at room temperature for 16 hrs. to afford 1.6 g (50%) of (S)—S-((E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-en-1-yl) 2-amino-3-methylbutanethioate benzenesulfonate as a white solid.

Example 4

Preparation of (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone) (Compound XX) from (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone) (Compound XIX).

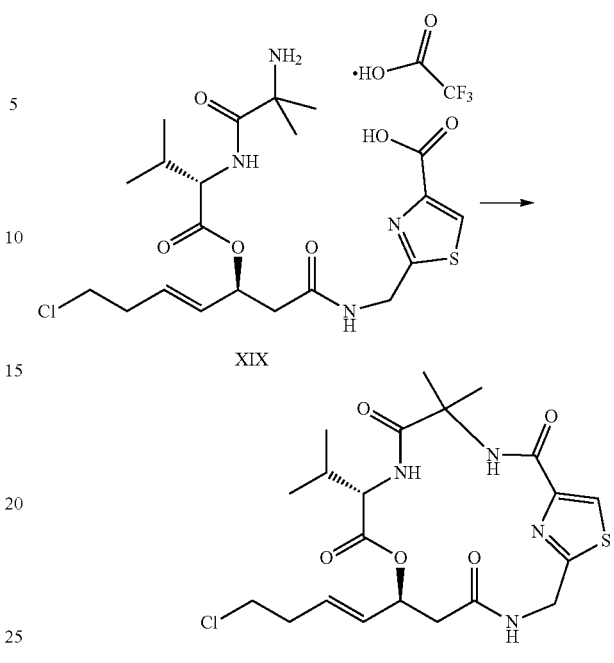

XIX

XX

HATU (26 g, 0.067 mol) was dissolved in acetonitrile (300 mL), and cooled to 0~5° C. A solution of 2-(((S,E)-3-(((S)-2-(2-amino-2-methylpropanamido)-3-methylbutanoyl)oxy)-7-chlorohept-4-enamido)methyl)thiazole-4-carboxylic acid trifluoroacetate (28 g crude from Example 5) and diisopropylethyl amine (40 ml, 0.225 mol) in dichloromethane (600 mL) and was added slowly dropwise to the HATU solution at 0~5° C. over 5-6 hours. After the addition, the mixture was stirred at 0~5° C. for an additional 2 hours at which time water (600 ml) was added. After layer separation, the aqueous layer was extracted twice with ethyl acetate (200 mL), and the combined organic layers were washed with brine, dried with anhydrous sodium sulfate and concentrated. Flash chromatography with silica gel (petroleum ether/ethyl acetate 50/50) provided 14.5 g (75% overall from tert-butyl 2-(((5S,8S)-5-((E)-4-chlorobut-1-en-1-yl)-8-isopropyl-11,11,15,15-tetramethyl-3,7,10,13-tetraoxo-6,14-dioxa-2,9,12-triazahexadecyl)thiazole-4-carboxylate) (from Example 5) of (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone) as a white solid. $^1$H NMR: (CDCl$_3$, 400 MHz): δ 8.05 (s, 1H), 7.69 (s, 1H), 6.61 (d, J=9.6 Hz, 1H), 6.41 (m, 1H), 5.83-5.73 (m, 3H), 5.19 (dd, J=17.2, 8.0 Hz, 1H), 4.67 (dd, J=9.6, 4.2 Hz, 1H), 4.36 (dd, J=17.6, 4.0 Hz, 1H), 3.56 (m, 2H), 2.75 (m, 2H), 2.52 (m, 2H), 2.34 (m, 1H), 1.91 (s, 3H), 1.64 (s, 3H), 0.93 (d, J=6.8 Hz, 3H), 0.75 (d, J=6.8 Hz, 3H).

Example 5

Preparation of (7S,10S)-10-((E)-4-chlorobut-1-en-1-yl)-7-isopropyl-4,4-dimethyl-9-oxa-16-thia-3,6,13,18-tetraazabicyclo[13.2.1]octadeca-1(17),15(18)-diene-2,5,8,12-tetraone) (Compound XIX) from 2-(((S,E)-3-(((S)-2-(2-amino-2-methylpropanamido)-3-methylbutanoyl)oxy)-7-chlorohept-4-enamido)methyl)thiazole-4-carboxylic acid trifluoroacetate (Compound XVIII).

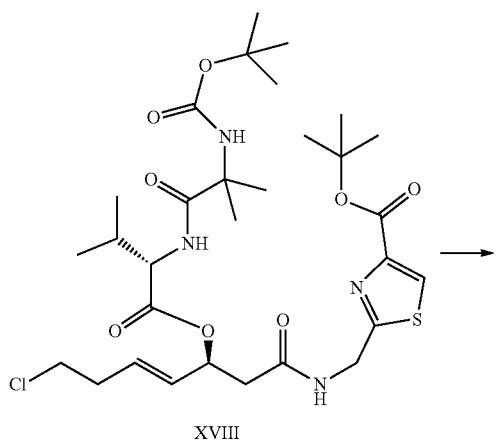

XVIII

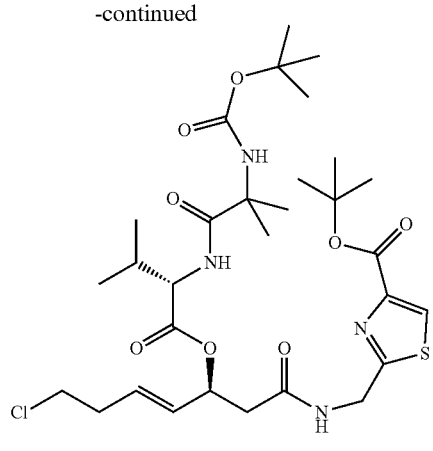

XVIII

Tert-butyl 2-(((S,E)-3-(((S)-2-amino-3-methylbutanoyl)oxy)-7-chlorohept-4-enamido)methyl)thiazole-4-carboxylate (20.0 g, 0.045 mol) and 2-((tert-butoxycarbonyl)amino)-2-methylpropanoic acid (8.4 g, 0.010 mol,) were dissolved in dichloromethane (200 mL). HATU (17.6 g, 0.048 mol) and diisopropylethyl amine (12 g, 0.096 mol) were successively added to the solution at 10-15° C. and stirring continued for 1 hour. 100 mL water was then added to the reaction mixture. The phases were separated and the aqueous phase was extracted with 100 mL dichloromethane. The combined organic phases were, dried with anhydrous sodium sulfate, filtered and concentrated to give 26.7 g (90%) of tert-butyl 2-((5S,8S)-5-((E)-4-chlorobut-1-en-1-yl)-8-isopropyl-11,11,15,15-tetramethyl-3,7,10,13-tetraoxo-6,14-dioxa-2,9,12-triazahexadecyl)thiazole-4-carboxylate acid trifluoroacetate which was used without further purification. $^1$H NMR: (CDCl$_3$, 400 MHz): δ 7.99 (s, 1H), 7.34 (bs, 1H), 7.15 (bs, 1H), 6.00 (bs, 1H), 5.80 (m, 1H), 5.65 (m, 1H), one extra proton in this region, took one proton out 4.94 (s, 1H), 4.75 (d, J=6.0 Hz, 2H), 4.23 (t, J=6.7 Hz, 1H), 3.50 (t, J=6.7 Hz, 2H), 2.65 (bs, 2H), 2.48 (q, J=6.7 Hz, 2H), 2.11 (m, 1H), 1.58 (s, 9H), 1.48-1.39 (m, 15H), 0.94 (d, J=6.8 Hz, 3H), 0.89 (d, J=6.8 Hz, 3H).

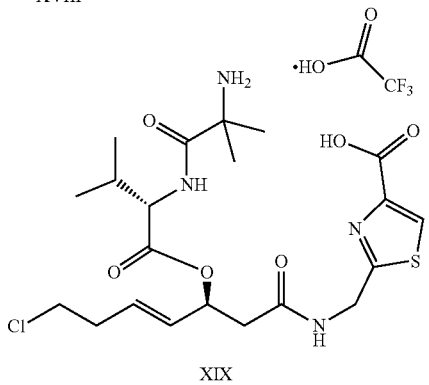

XIX

Tert-butyl 2-((5S,8S)-5-((E)-4-chlorobut-1-en-1-yl)-8-isopropyl-11,11,15,15-tetramethyl-3,7,10,13-tetraoxo-6,14-dioxa-2,9,12-triazahexadecyl)thiazole-4-carboxylate (28 g, 0.04 mol) was dissolved in dichloromethane (300 ml), and trifluoroacetic acid (150 mL) was added. The mixture was stirred at room temperature for 20 hours and then concentrated to dryness. The crude 2-(((S,E)-3-(((S)-2-(2-amino-2-methylpropanamido)-3-methylbutanoyl)oxy)-7-chlorohept-4-enamido)methyl)thiazole-4-carboxylic acid trifluoroacetate thus obtained was used directly in next step (Example 4) without purification.

Example 6

Preparation of tert-butyl 2-((5S,8S)-5-((E)-4-chlorobut-1-en-1-yl)-8-isopropyl-11,11,15,15-tetramethyl-3,7,10,13-tetraoxo-6,14-dioxa-2,9,12-triazahexadecyl)thiazole-4-carboxylate acid trifluoroacetate (Compound XVIII) from tert-butyl 2-(((S,E)-3-(((S)-2-amino-3-methylbutanoyl)oxy)-7-chlorohept-4-enamido)methyl)thiazole-4-carboxylate (Compound XVII) and 2-((tert-butoxycarbonyl)amino)-2-methylpropanoic acid (Compound VII).

Example 7

Preparation of tert-butyl 2-(((S,E)-3-(((S)-2-amino-3-methylbutanoyl)oxy)-7-chlorohept-4-enamido)methyl)thiazole-4-carboxylate (Compound XVII) from tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate (Compound XVI).

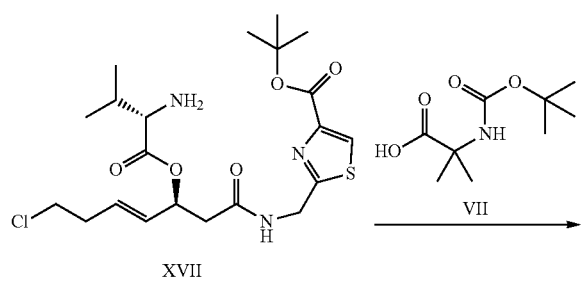

XVII

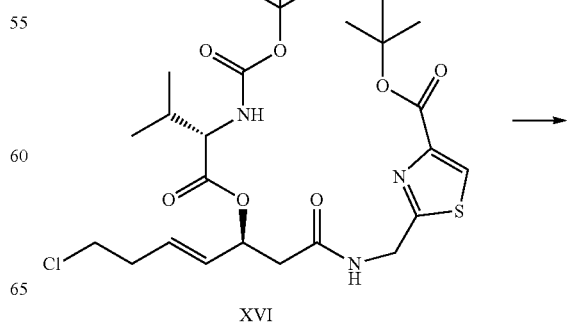

XVI

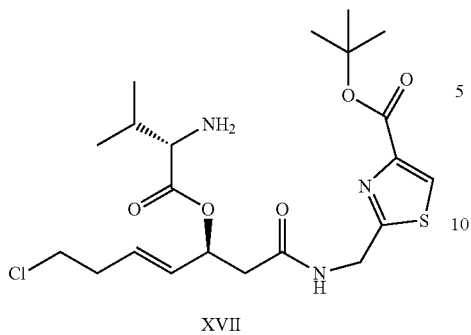

XVII

To a solution of tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate (27.0 g, 8 mmol) in dioxane (20 mL) at 5-10° C. was added 4M HCl in dioxane (20 mL). The mixture was stirred at 5-10° C. for 3 hours and slowly poured into a cooled, saturated sodium carbonate solution. The resulting mixture was extracted twice with 100 mL of ethyl acetate, and the combined organic layers were washed with brine, dried with anhydrous sodium sulfate and concentrated to give 22.3 g (100%) of tert-butyl 2-(((S,E)-3-(((S)-2-amino-3-methylbutanoyl)oxy)-7-chlorohept-4-enamido)methyl)thiazole-4-carboxylate as a pale yellow oil which was used directly in next step (Example 6) without further purification.

Example 8

Preparation of tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate (Compound VIII) from (S,E)-tert-butyl 2-((7-chloro-3-hydroxyhept-4-enamido)methyl)thiazole-4-carboxylate (Compound VI-B) and 2-((tert-butoxycarbonyl)amino)-2-methylpropanoic acid (Compound VII).

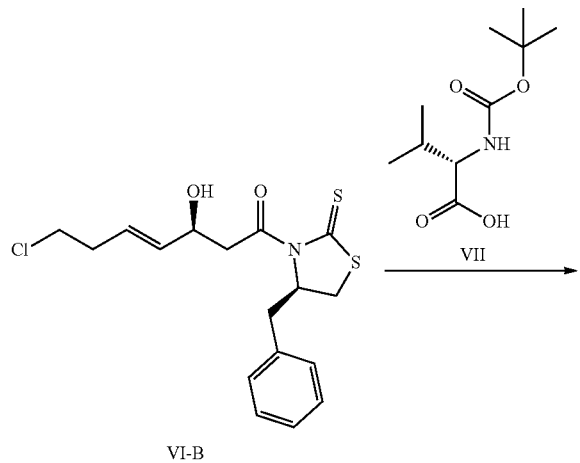

VI-B

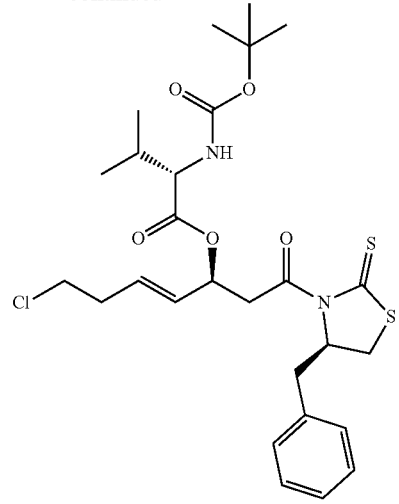

VIII

To solution of (S,E)-1-((R)-4-benzyl-2-thioxothiazolidin-3-yl)-7-chloro-3-hydroxyhept-4-en-1-one (2.0 g, 5.4 mmol) in dichloromethane (20 mL) was added (S)-2-((tert-butoxycarbonyl)amino)-3-methylbutanoic acid (1.41 g; 6.5 mmol), dicyclohexylcarbodiimide (1.34 g; 6.5 mmol) and dimethylamino pyridine (66 mg; 0.54 mmol) at 10-15° C. for 3 hours. The reaction was then filtered to remove solids and the filtrate was washed with water (10 mL), dried with anhydrous sodium sulfate and concentrated. The crude product was purified by column chromatography using silica gel (petroleum ether/ethyl acetate 25/1) to give 1.8 g (59%) of (S)—(S,E)-1-((R)-4-benzyl-2-thioxothiazolidin-3-yl)-7-chloro-1-oxohept-4-en-3-yl 2-((tert-butoxycarbonyl)amino)-3-methylbutanoate as a yellow, foamy solid.

$^1$H NMR: (CDCl$_3$, 400 MHz). δ 7.37-7.27 (m, 5H), 5.93-5.83 (m, 2H), 5.62 (dd, J=15.8, 8.6 Hz, 1H), 5.37 (m, 1H), 5.04 (d, J=9.1 Hz, 1H), 4.19 (dd, J=9.0, 4.5 Hz, 1H), 3.68 (dd, J=17.4, 8.6 Hz, 1H), 3.57 (dd, J=18.8, 4.7 Hz, 1H), 3.54 (t, J=6.8 Hz, 2H), 3.45 (dd, J=11.5, 7.2 Hz, 1H), 3.21 (dd, J=13.1, 3.5 Hz, 1H), 3.02 (dd. J=13.0, 10.7 Hz, 1H), 2.89 (d, J=11.6 Hz, 1H), 2.51 (q, J=6.8 Hz, 2H), 2.12 (m, 1H), 1.42 (s, 9H), 0.95 (d, J=6.8 Hz, 3H), 0.85 (d, J=6.9 Hz, 3H).

Example 9

Preparation of (S)—(S,E)-1-((R)-4-benzyl-2-thioxothiazolidin-3-yl)-7-chloro-1-oxohept-4-en-3-yl 2-((tert-butoxycarbonyl)amino)-3-methylbutanoate (Compound XVI) from tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate (Compound VIII) and tert-butyl 2-(aminomethyl)thiazole-4-carboxylate (Compound XV).

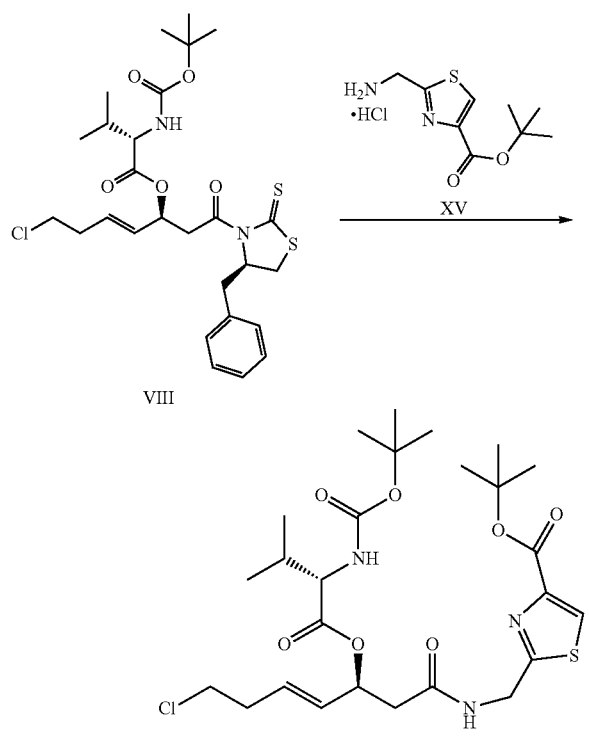

VIII

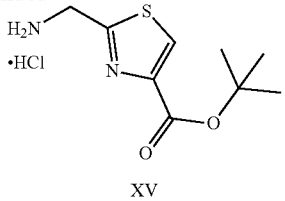

XV

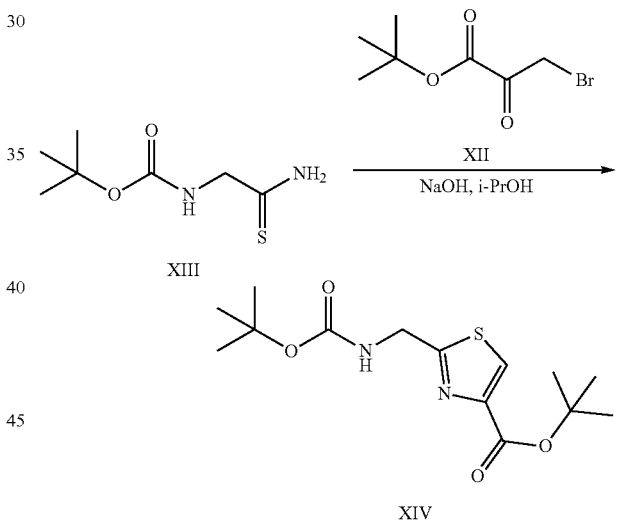

XVI

To a solution of (S)—(S,E)-1-((R)-4-benzyl-2-thioxothiazolidin-3-yl)-7-chloro-1-oxohept-4-en-3-yl 2-((tert-butoxycarbonyl)amino)-3-methylbutanoate (0.5 g, 0.88 mmol) in DMF (5 mL), was added tert-butyl 2-(aminomethyl)thiazole-4-carboxylate hydrochloride (0.19 g, 0.88 mmol) and diisopropylethyl amine (340 mg, 2.64 mmol), and the resulting mixture was stirred at 10-15° C. for 3 hours. H₂O (20 mL) was then added and the resulting mixture was extracted with ethyl acetate (50 mL). The organic phase was separated, dried with anhydrous sodium sulfate and concentrated. The crude product was purified by column chromatography using silica gel (petroleum ether/ethyl acetate 2/1) to give 0.40 g (80%) of tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate as a foamy, white solid. ¹H NMR: (CDCl₃, 400 MHz): δ 7.98 (s, 1H), 7.48 (bs, 1H), 7.13 (bs, 1H), 5.80 (m, 1H), 5.62 (m, 2H), 4.97 (s, 1H), 4.75 (d, J=5.9 Hz, 2H), 4.24 (t, J=6.7 Hz, 1H), 3.49 (t, J=6.7 Hz, 2H), 2.65 (d, J=4.9 Hz, 2H), 2.47 (q, J=6.7 Hz, 2H), 2.08 (m, 11H) 1.57 (s, 9H), 1.41 (s, 9H), 0.92 (d, J=6.8 Hz, 3H), 0.87 (d, J=6.8 Hz, 3H).

Example 10

Preparation of tert-butyl 2-((amino)methyl)thiazole-4-carboxylate (Compound XV) from tert-butyl 2-(((tert-butoxycarbonyl)amino)methyl)thiazole-4-carboxylate (Compound XIV).

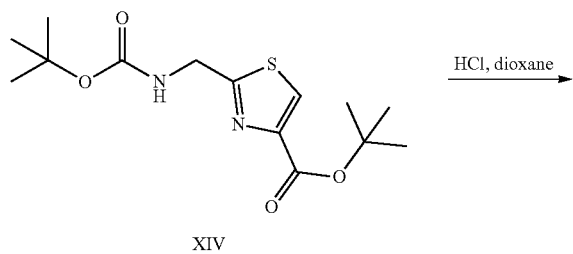

XIV

-continued

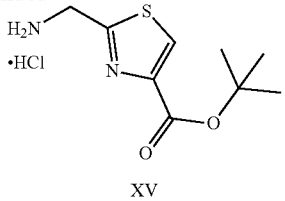

XV

To a solution of 20.0 g (0.064 mol) of tert-butyl 2-(((tert-butoxycarbonyl)amino)methyl)thiazole-4-carboxylate in dioxane (160 ml) at room temperature was added 120 ml 4M HCl in dioxane. After stirring overnight at room temperature, 160 ml petroleum ether was added and the resulting precipitate was filtered, washed with heptane and dried under vacuum to give 15.9 g (100%) of tert-butyl 2-(aminomethyl)thiazole-4-carboxylate hydrochloride which was used without further purification. ¹H NMR: (CD₃OD, 400 MHz): δ 8.20 (s, 9H), 4.84 (bs, 1H), 4.13 (s, 2H), 1.61 (s, 9H).

Example 11

Preparation of tert-butyl 2-(((tert-butoxycarbonyl)amino)methyl)thiazole-4-carboxylate (Compound XIV) from tert-butyl bromopyruvate (Compound XII) and tert-butyl (2-amino-2-thioxoethyl)carbamate (Compound XIII).

28.0 g (0.126 mol) of ethyl bromopyruvate and 25.0 g (0.131 mol) of tert-butyl (2-amino-2-thioxoethyl)carbamate were combined in isopropanol (250 ml). The mixture was stirred for 16 h. at which time 28.6 g of 20% aqueous sodium hydroxide was added followed by 500 ml H₂O. The product was extracted with EA (500 ml, 250 ml). The organic layer was washed with saturated sodium chloride solution, dried with anhydrous sodium sulfate, filtered and dried. Flash chromatography using silica gel (petroleum ether/ethyl acetate 85/15) gave 32 g, 72%) of tert-butyl 2-(((tert-butoxycarbonyl)amino)methyl)thiazole-4-carboxylate as a white solid. ¹H NMR: (CD₂Cl₂, 400 MHz): δ 7.92 (s, 1H), 5.23 (bs, 1H), 1.37 (s, 9H), 1.53 (s, 9H).

Example 12

Preparation of (S,E)-1-((R)-4-benzyl-2-thioxothiazolidin-3-yl)-7-chloro-3-hydroxyhept-4-en-1-one (Compound XI)

from (S,E)-1-((R)-4-benzyl-2-thioxothiazolidin-3-yl)-7-chloro-3-hydroxyhept-4-en-1-one (Compound VI-B) and tert-butyl 2-(aminomethyl)thiazole-4-carboxylate (Compound XV).

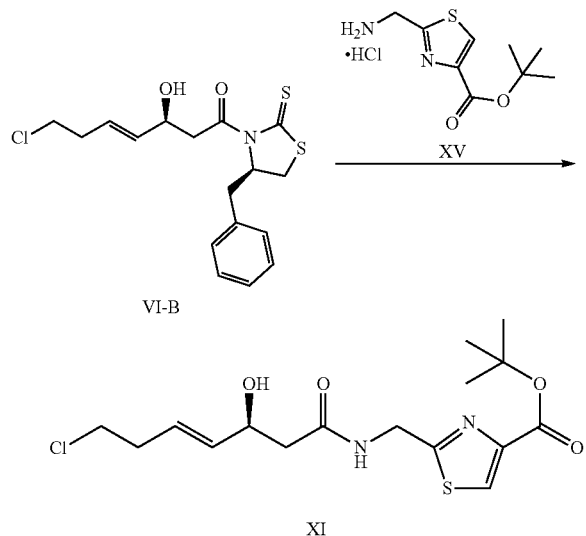

To a solution of (S,E)-1-((R)-4-benzyl-2-thioxothiazolidin-3-yl)-7-chloro-3-hydroxyhept-4-en-1-one (10.0 g, 0.027 mol) in dichloromethane (80 mL) was added tert-butyl 2-(aminomethyl)thiazole-4-carboxylate (8.0 g, 0.032 mol). Diisopropylethyl amine (9.0 g, 0.07 mol) was then added dropwise while maintaining the temperature between 20-30° C. After the addition, the resulting solution was stirred at room temperature for 8 hours, at which time water (80 mL) was added. The layers were separated, and the aqueous layer was extracted once with dichloromethane (40 ml). The combined organic layers were washed with brine, dried with anhydrous sodium sulfate and concentrated. The residue was dissolved in ethyl acetate (20 mL) and the precipitated solid was filtered. The mother liquor was concentrated, the residue was dissolved in ethyl acetate (20 mL), and the precipitated solid was filtered. The combined solids were dried under vacuum to give 7.8 g (77%) of (S,E)-tert-butyl 2-((7-chloro-3-hydroxyhept-4-enamido)methyl)thiazole-4-carboxylate. An additional 1.3 g of product was obtained by concentrating the final mother liquor and purifying the residue by flash chromatography with silica gel (petroleum ether/dichloromethane: 80/20~50/50). $^1$H NMR: (CDCl$_3$, 400 MHz): δ 7.98 (s, 1H), 7.38 (bt, J=5.7 Hz, 1H), 5.72 (dt, J=15.6, 5.6 Hz, 1H), 5.61 (dd. J=15.6, 5.8 Hz, 1H), 4.75 (dq, J=15.6, 6.0 Hz, 2H), 4.54 (bs, 1H), 3.93 (s, 1H), 3.50 (t, J=6.8 Hz, 2H), 2.57-2.43 (m, 4H), 1.57 (s, 9H).

Example 13

Preparation of (S)—(S,E)-1-((R)-4-benzyl-2-thioxothiazolidin-3-yl)-7-chloro-1-oxohept-4-en-3-yl 2-(tert-butoxycarbonyl)amino)-3-methylbutanoate (Compound XVI) from (S,E)-1-((R)-4-benzyl-2-thioxothiazolidin-3-yl)-7-chloro-3-hydroxyhept-4-en-1-one (Compound XI) and 2-((tert-butoxycarbonyl)amino)acetic acid (Compound VII).

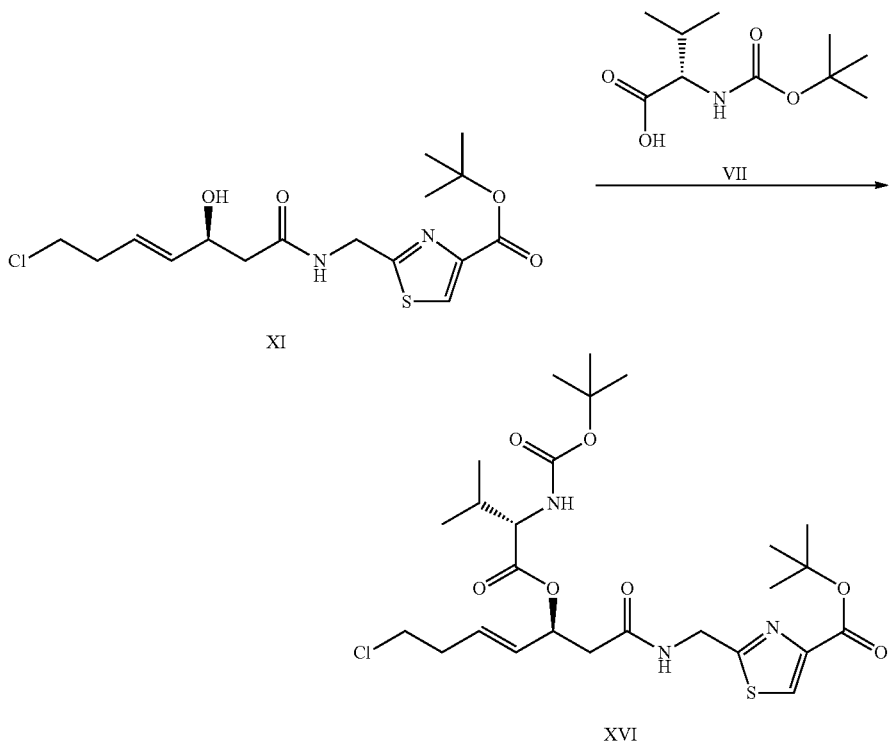

(S,E)-1-((R)-4-benzyl-2-thioxothiazolidin-3-yl)-7-chloro-3-hydroxyhept-4-en-1-one (17.0 g, 0.045 mol) and (S)-2-((tert-butoxycarbonyl)amino)-3-methylbutanoic acid (11.8, 0.045 mol) were dissolved in dichloromethane (250 mL), the mixture was cooled to 0-5° C. and dimethylaminopyridine (0.55 g, 4.5 mmol) and 1-ethyl-3-(3-dimethylaminopropyl) carbodiimide (17.3 g, 0.054 mol) were added. The reaction was stirred at 0-5° C. for 20 hours at which time dichloromethane (100 mL) water (200 mL) were added. The organic layer was separated and washed with water (150 mL). The organic layer was dried with anhydrous sodium sulfate and concentrated to give 25.8 g (100%) of (S)—(S, E)-1-((R)-4-benzyl-2-thioxothiazolidin-3-yl)-7-chloro-1-oxohept-4-en-3-yl 2-((tert-butoxycarbonyl)amino)-3-methylbutanoate as a foamy solid which was used without further purification. $^1$H NMR: (CD$_2$Cl$_2$, 400 MHz): δ 7.98 (s, 1H), 7.49 (bs, 1H), 7.13 (bs, 1H), 5.78 (m, 1H), 5.65 (m, 1H), 4.98 (s, 1H), 4.75 (d, J=2.8 Hz, 2H), 4.25 (t. J=6.4 Hz, 2H), 3.49 (t, J=6.8 Hz, 2H), 2.65 (d, J=6.8 Hz, 2H), 2.47 (q, J=6.4 Hz, 4H), 1.57 (s, 9H), 1.41 (s, 9H), 0.92 (d, J=6.8 Hz, 3H) 0.88 (d, J=6.8 Hz, 3H).

Example 14a

Preparation of (S,E)-7-chloro-3-hydroxy-1-((R)-4-isopropyl-2-thioxothiazolidin-3-yl)hept-4-en-1-one (Compound VI-A-1, Table 2) from (E)-5-chloropent-2-enal (Compound IV) and (R)-1-(4-isopropyl-2-thioxothiazolidin-3-yl)ethanone (Compound V-A; Table 2) (from Scheme 3).

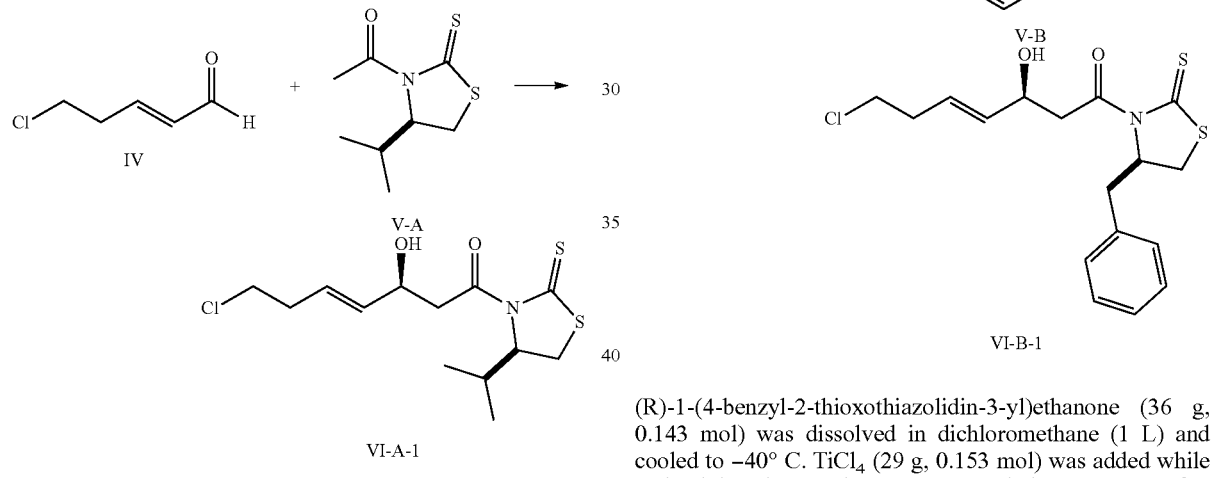

(R)-1-(4-isopropyl-2-thioxothiazolidin-3-yl)ethanone (4.0 g, 19.6 mmol) was dissolved in dichloromethane (150 ml) and cooled to −40° C. TiCl$_4$ (6.0 g, 31.62 mmol) was added while maintaining the reaction temperature below −40° C. After stirring for 1 h, diisopropylethyl amine (4.1 g, 31.62 mmol) was added dropwise while maintaining the reaction temperature between −40 to −50° C. After the addition, the mixture was stirred at −40° C. for 2 hours at which time, the reaction was cooled to −78° C. and (E)-5-chloropent-2-enal (2.21 g, 18.6 mmol) in dichloromethane (10 ml) was added slowly dropwise while maintaining the reaction temperature below −65° C. After the addition, the resulting mixture was stirred at −70 to −65° C. for 1 hour and then poured into a mixture of saturated aqueous ammonium chloride solution (100 ml) and saturated aqueous sodium chloride (100 ml). The resulting mixture was extracted twice with dichloromethane (400 ml) and the combined organic layers were washed with saturated aqueous sodium chloride solution (100 mL) and concentrated to dryness. Purification by column chromatography gave 4.8 g (80%) of (S,E)-7-chloro-3-hydroxy-1-((R)-4-isopropyl-2-thioxothiazolidin-3-yl)hept-4-en-1-one (Compound VC-A, Table 2). $^1$H NMR: (CDCl$_3$, 400 MHz): δ 5.76 (dt, J=15.6, 6.5 Hz, 1H), 5.66 (dd, J=15.6, 5.6 Hz, 1H), 5.15 (t, J=7.0 Hz, 1H), 4.65 (m, 1H), 3.64 (dd, J=17.6, 3.0 Hz, 1H). 3.56-3.50 (m, 3H), 3.29 (dd, J===17.7, 8.8 Hz, 1H) 3.03 (d, J=11.5 Hz, 1H), 2.90 (bs, 1H), 2.51 (q, J=6.8 Hz, 2H), 2.36 (m, 1H), 1.06 (d, J=6.8 Hz, 3H), 0.98 (d, J=6.9 Hz, 3H).

Example 14b

Preparation (S,E)-1-((R)-4-benzyl-2-thioxothiazolidin-3-yl)-7-chloro-3-hydroxyhept-4-en-1-one (Compound VI-B-1; Table 2) from (E)-5-chloropent-2-enal (Compound IV) and (R)-1-(4-benzyl-2-thioxothiazolidin-3-yl)ethanone (Compound V-B)(from

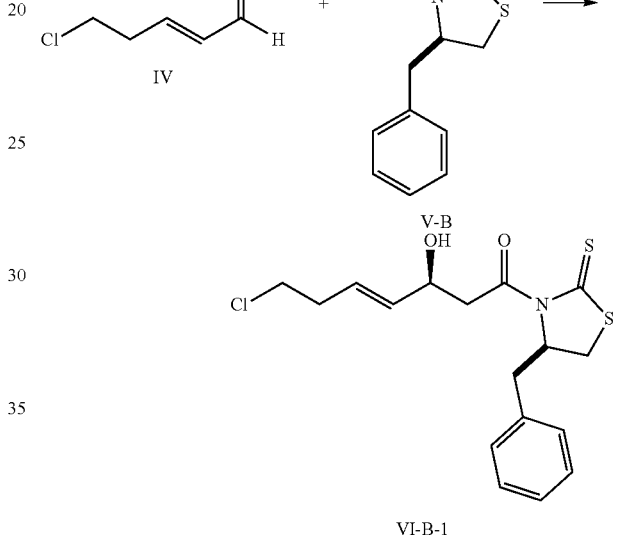

(R)-1-(4-benzyl-2-thioxothiazolidin-3-yl)ethanone (36 g, 0.143 mol) was dissolved in dichloromethane (1 L) and cooled to −40° C. TiCl$_4$ (29 g, 0.153 mol) was added while maintaining the reaction temperature below −40° C. After stirring for 1 h, diisopropylethyl amine (20 g, 0.153 mol) was added dropwise while maintaining the reaction temperature between −40 to −50° C. After the addition, the mixture was stirred at −40° C. for 2 hours at which time, the reaction was cooled to −78° C. and (E)-5-chloropent-2-enal (10.0 g, 0.084 mol) in dichloromethane (40 ml) was added slowly dropwise while maintaining the reaction temperature below −65° C. After the addition, the resulting mixture was stirred at −70 to −65° C. for 1 hour and then poured into a mixture of saturated aqueous ammonium chloride solution (500 ml) and saturated aqueous sodium chloride (500 ml). The resulting mixture was extracted twice with dichloromethane (400 ml) and the combined organic layers were washed with saturated aqueous sodium chloride solution (500 mL) and concentrated to dryness. Ethyl acetate (50 mL) was added to the residue, followed by a slow addition of petroleum ether (150 mL). The precipitated solid was collected by filtration and the mother liquor was concentrated. Ethyl acetate (50 mL) was added to the residue, followed by a slow addition of petroleum ether (150 mL). The precipitated solid was collected by filtration, combined with the first lot of collected solid and dried under vacuum to give 22 g (71%) of (S,E)-1-((R)-4-benzyl-2-thioxothiazolidin-3-yl)-7-chloro-3-hydroxyhept-4-en-1-one (Compound VI-B-1, Table 2) which contained 2% of the minor diastereomer (R,E)-1-((R)-4-benzyl-2-thioxothiazolidin-3-yl)-7-chloro-3-hydroxyhept-4-en-1-one (Compound VI-B, Table 2). ¹H NMR: (CDCl₃, 400 MHz): δ 7.38-7.27 (m, 5H), 5.78 (dt, 1H, J=16.1, 6.3 Hz, 1H), 5.69 (dd, J=15.5, 5.6 Hz, 1H), 5.39 (ddd, J=10.4, 6.9, 3.8 Hz, 1H), 4.68 (m, 1H), 3.65 (dd. J=17.7, 2.9 Hz, 1H), 3.57 (t, J=6.8 Hz, 2H), 3.41 (dd, J=11.5, 7.2 Hz, 1H), 3.31 (dd, J=17.7, 8.9 Hz, 1H), 3.23 (dd, J=13.2, 3.9 Hz, 1H), 3.05 (dd, J=13.2, 10.5 Hz, 1H), 2.91 (d, J=11.6 Hz, 1H), 2.81 (d, J=4.4 Hz, 1H), 2.54 (q, J=6.7 Hz, 2H).

Example 15

Preparation of (E)-5-chloropent-2-enal (Compound IV) from 4-chloro-but-1-ene (Compound I) and crotonaldehyde, (Compound II).

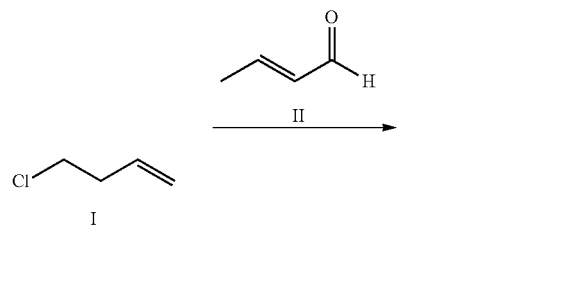

4-chloro-but-1-ene (20 g, 0.22 mol), crotonaldehyde (23 g, 1.5 eq) and CuI (2.5 g, 0.06 eq) were combined in dichloromethane (400 mL) and (1,3-bis(2,4,6-trimethylphenyl)-2-imidazolidinylidene)dichloro(phenvlmethylene)(tricyclohexylphosphine)ruthenium)(Grubbs 2nd generation olefin metathesis catalyst) (0.011 mol, 0.93 g, 0.5 mol %) was added in one portion while purging with nitrogen. The mixture was heated to reflux at 40° C. for 16 hours with stirring at which time analysis of the reaction by 1 HNMR indicated 65-70% conversion. The reaction mixture was then cooled, filtered, and concentrated. The residue was dissolved in dichloromethane (150 ml) and the dichloromethane was evaporated under vacuum to remove unreacted starting material. This was repeated 4 times. The product thus produced was used in subsequent Aldol condensation reactions without any further purification. An analytically pure sample was obtained via flash chromatography using silica gel (petroleum ether/dichloromethane 50/50). ¹H NMR: (CD₂Cl₂, 400 MHz): δ 9.51 (d, J=8.0 Hz, 1H), 6.82 (dt, J=15.6, 6.8 Hz, 1H), 6.16 (ddt, J=15.6, 6.8, 1.6 Hz, 1H), 3.68 (t, J=6.4 Hz, 2H), 2.78 (qd, J=5.2, 1.2 Hz, 2H).

Example 16

Preparation of (E)-5-chloropent-2-en-1-ol (Compound III) from 4-chloro-but-1-ene (Compound I) and (E)-but-2-ene-1,4-diol, (Compound II from Scheme 1).

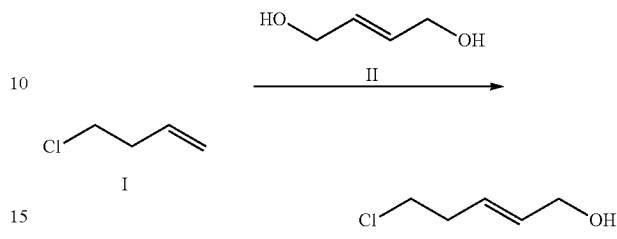

4-chloro-but-1-ene (3.4 g, 0.037 mol), (E)-but-2-ene-1,4-diol (5.0 g, 0.055 mol) and CuI (0.42 g, 2.22 mmol) were combined in dichloromethane (70 mL) and (1,3-bis(2,4,6-trimethylphenyl)-2-imidazolidinylidene)dichloro(phenylmethylenextricyclohexylphosphine)ruthenium Grubbs 2nd generation olefin metathesis catalyst) (0.185 mmol, 0.157 g) was added in one portion while purging with nitrogen. The mixture was heated to reflux at 40° C. for 16 hours with stirring at which time analysis of the reaction by 1HNMR indicated 82% conversion. The reaction mixture was then cooled, filtered, and concentrated to give crude (E)-5-chloropent-2-en-1-ol which was used directly in the next reaction. ¹H NMR: (DMSO-d₆, 400 MHz): δ 5.69-5.52 (m, 2H), 4.70 (t, J=5.4 Hz, 1H), 3.91 (m, 2H), 3.64 (t, J=6.8 Hz, 2H), 2.54 (m, 2H).

Example 17

Preparation of (E)-5-chloropent-2-en-1-al from (Compound IV) from (E)-5-chloropent-2-en-1-ol (Compound I).

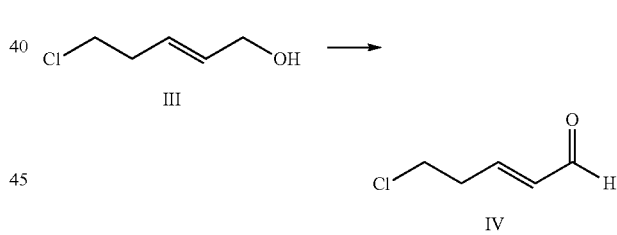

To a solution of (E)-5-chloropent-2-en-1-ol (0.40 g, 3.33 mmol) in dichloromethane (5 mL) was added manganese dioxide (0.87 g, 10.0 mmol) and the resulting mixture was stirred at room temperature for 20 hours. The mixture was then filtered and concentrated to give of (E)-5-chloropent-2-en-1-al (90% conversion based on ¹H NMR). ¹H NMR: (CD₂Cl₂, 400 MHz): δ 9.51 (d, J=8.0 Hz, 1H), 6.82 (dt, J=15.6, 6.8 Hz, 1H), 6.16 (ddt, J=15.6, 6.8, 1.6 Hz, 1H), 3.68 (t, J=6.4 Hz, 2H), 2.78 (qd, J=5.2, 1.2 Hz, 2H).

Example 18

Preparation of S-((E)-4-((5R,8S,11S)-8-isopropyl-5-methyl-6,9,13-trioxo-10-oxa-3,17-dithia-7,14,19,20-tetraazatricyclo[14.2.1.1²,⁵]icosa-1(18),2(20),16(19)-trien-11-yl)but-3-en-1-yl) octanethioate (Largazole, a compound of Formula (2)) from (5R,8S,11S)-11-((E)-4-chlorobut-1-en-1-yl)-8-isopropyl-5-methyl-10-oxa-3,17-dithia-7,14,19,20-tetraazatricyclo[14.2.1.1²,⁵]icosa-1(18),2(20),16(19)-triene-6,9,13-trione (Compound XXIX).

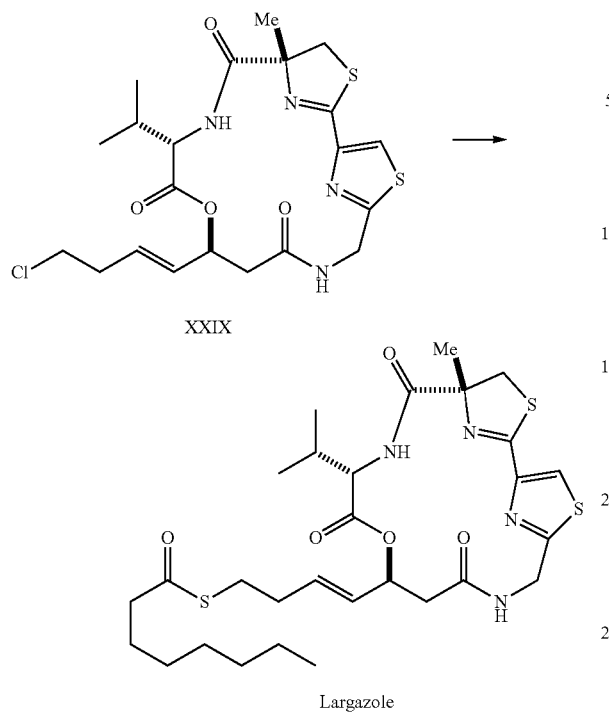

XXIX

Largazole

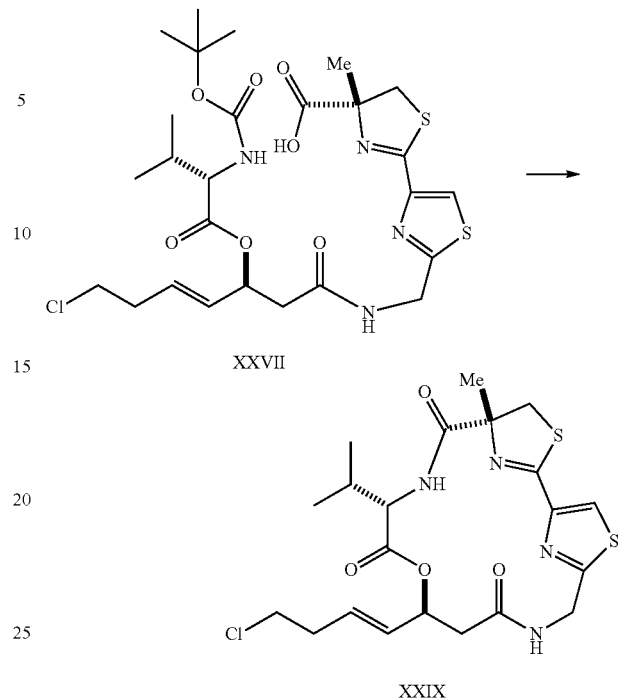

XXVII

XXIX (5R,8S,11S)-11-((E)-4-chlorobut-1-en-1-yl)-8-isopropyl-5-methyl-10-oxa-3,17-dithia-7,14,19,20-tetraazatricyclo[14.2.1.12,5]icosa-1(18),2(20),16(19)-triene-6,9,13-trione (Compound XXIX) (0.23 g, 0.46 mmol), octanethioic S-acid (0.44 g, 2.75 mmol), potassium carbonate (0.40 g, 2.90 mmol) and potassium iodide (0.067 g, 0.41 mmol) were dissolved in acetonitrile (20 mL) at room temperature. The mixture was stirred at room temperature under nitrogen for 16 hours. The mixture was filtered, concentrated and purified by preparative silica gel chromatography (dichloromethane/methanol 50/1) to give 0.12 g, (42%) of S-((E)-4-((5R,8S,11S)-8-isopropyl-5-methyl-6,9,13-trioxo-10-oxa-3,17-dithia-7,14,19,20-tetraazatricyclo[14.2.1.12,5]icosa-1(18),2(20),16(19)-trien-11-yl)but-3-en-1-yl) octanethioate as a white solid. $^1$H NMR: (CDCl$_3$, 400 MHz): δ 7.76 (s, 1H), 7.16 (d, J=9.4 Hz, 1H), 6.43 (d, J=10.4 Hz, 1H), 5.83 (dt, J=15.8, 7.3 Hz, 1H), 5.66 (m, 1H), 5.51 (dd, J=15.5, 6.9 Hz, 1H), 5.29 (dd, J=17.7, 9.3 Hz, 1H), 4.60 (dd, J=9.4, 3.3 Hz, 1H), 4.27 (dd, J=17.6, 3.0 Hz, 1H), 4.04 (d, J=11.4 Hz, 1H), 3.28 (d, J=11.4 Hz, 1H), 2.90 (t, J=7.2 Hz, 2H), 2.87 (dd, J=16.4, 10.4 Hz, 1H), 2.68 (dd, J=16.3, 2.7 Hz, 1H), 2.53 (t, J=7.5 Hz, 1H), 2.31 (q, J=7.0 Hz, 2H), 2.11 (m, 1H), 1.87 (s, 3H), 1.62 (m, 2H), 1.27 (m, 8H), 0.87 (m, 3H), 0.69 (d, J=6.7 Hz, 3H), 0.51 (d, J=6.8 Hz, 3H).

Example 19

Preparation of (5R,8S,11S)-11-((E)-4-chlorobut-1-en-1-yl)-8-isopropyl-5-methyl-10-oxa-3,17-dithia-7,14,19,20-tetraazatricyclo[14.2.1.12,5]icosa-1(18),2(20),16(19)-triene-6,9,13-trione (Compound XXIX) from (R)-2'-((5S,8S)-5-((E)-4-chlorobut-1-en-1-yl)-8-isopropyl-12,12-dimethyl-3,7,10-trioxo-6,11-dioxa-2,9-diazatridecyl)-4-methyl-4,5-dihydro-[2,4'-bithiazole]-4-carboxylic acid (Compound XXVII).

(R)-2'-((5S,8S)-5-((E)-4-chlorobut-1-en-1-yl)-8-isopropyl-12,12-dimethyl-3,7,10-trioxo-6,11-dioxa-2,9-diazatridecyl)-4-methyl-4,5-dihydro-[2,4'-bithiazole]-4-carboxylic acid (Compound XXVII)(1.5 g, 2.4 mmol) was dissolved in dichloromethane (20 ml), and trifluoroacetic acid (2.9 g, 25.4 mmol) was added while stirring at 20-25° C. After stirring the resulting mixture at 20-25° C. for 3 hours, an additional aliquot of trifluoroacetic acid (0.80 g, 7.0 mmol) was added and the resulting mixture was stirred for an additional 3.5 hours at which time the reaction was determined to be complete by HPLC. To the crude reaction mixture containing (R)-2'-(((SE)-3-(((S)-2-amino-3-methylbutanoyl)oxy)-7-chlorohept-4-enamido)methyl)-4-methyl-4,5-dihydro-[2,4'-bithiazole]-4-carboxylic acid trifluoroacetic acid salt (Compound XXVIII) was added diisopropylethyl amine (4.7 g, 41.2 mmol). The resulting mixture was then added slowly dropwise over a 5-6 hour period to a preformed solution of HATU (2.9 g, 7.63 mmol) dissolved in acetonitrile (50 mL) at 0-5° C. After the addition, the mixture was stirred at 0-5° C. for an additional 2 hours at which time water (100 mL) was added. After layer separation, the aqueous layer was extracted twice with ethyl acetate (50 mL), and the combined organic layers were washed with brine, dried with anhydrous sodium sulfate and concentrated. Flash chromatography with silica gel (dichloromethane/methanol 40/1) provided (5R,8S,11S)-11-((E)-4-chlorobut-1-en-1-yl)-8-isopropyl-5-methyl-10-oxa-3,17-dithia-7,14,19,20-tetraazatricyclo[14.2.1.12,5]icosa-1(18),2(20),16(19)-triene-6,9,13-trione (0.26 g) as a white solid (23% overall from Compound XXVII). $^1$H NMR: (CDCl$_3$, 400 MHz): δ 7.76 (s, 1H), 7.19 (d, J=7.4 Hz, 1H), 6.49 (d, J=8.6 Hz, 1H), 5.89 (dt, J=15.7, 7.3 Hz, 1H), 5.70 (m, 1H), 5.60 (dd, J=15.6, 6.5 Hz, 1H), 5.28 (dd, J=17.0, 9.1 Hz, 1H), 4.61 (dd, J=9.0, 3.5 Hz, 1H), 4.27 (dd, J=17.5, 2.9 Hz, 1H), 4.04 (d, J=11.2 Hz, 1H), 3.54 (t, J=6.6 Hz, 2H), 3.28 (d, J=11.3 Hz, 1H), 2.85 (m, 1H), 2.72 (dd, J=16.3, 2.7 Hz, 1H), 2.51 (q, J=6.7 Hz, 2H), 2.10 (m, 1H), 1.86 (s, 3H), 0.70 (d, J=6.9 Hz, 3H), 0.53 (d, J=6.8 Hz, 3H).

Example 20

Preparation of (R)-2'-((5S,8S)-5-((E)-4-chlorobut-1-en-1-yl)-8-isopropyl-12,12-dimethyl-3,7,10-trioxo-6,11-dioxa-2,9-diazatridecyl)-4-methyl-4,5-dihydro-[2,4'-bithiazole]-4-carboxylic acid (Compound XXVII) from tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate (Compound VIII) and (R)-2'-(aminomethyl)-4-methyl-4,5-dihydro-[2,4'-bithiazole]-4-carboxylic acid (Compound XXVI).

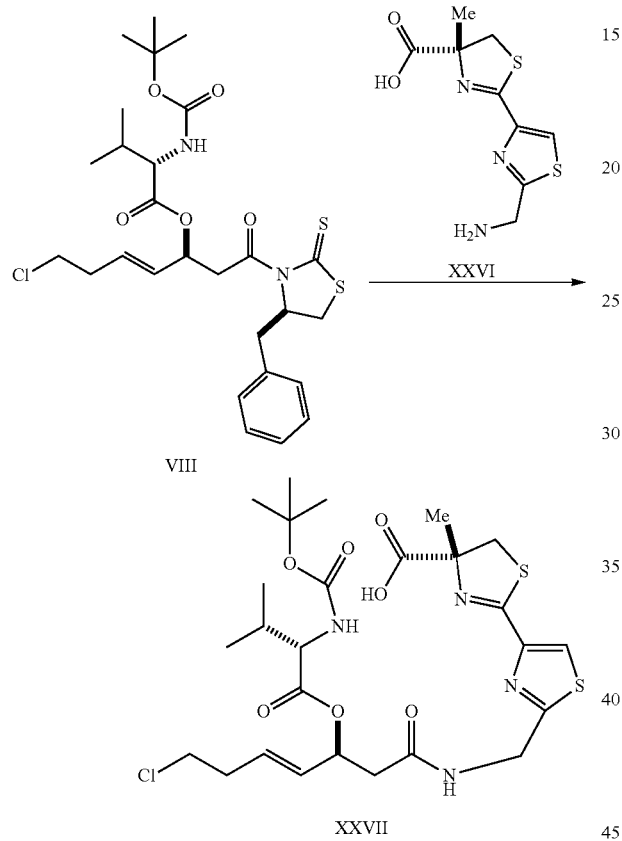

Tert-butyl 2-((5S,8S)-5-((E)-4-chlorobut-1-en-1-yl)-8-isopropyl-12,12-dimethyl-3,7,10-trioxo-6,11-dioxa-2,9-diazatridecyl)thiazole-4-carboxylate (Compound VIII)(1.0 g, 1.8 mmol) was added to a preformed solution of (R)-2'-(aminomethyl)-4-methyl-4,5-dihydro-[2,4'-bithiazole]-4-carboxylic acid trifluoroacetic acid salt (Compound XXVI) (0.51 g, 2.0 mmol) (prepared via modification of the method described in: Xiao, Q. et al., *Journal of Asian Natural Products Research*, (2010), 12:11, 940) and diisopropylethylamine (2.5 g, 0.025 mmol) in dichloromethane (10 mL). After stirring at 25° C. for 16 hours, 1-0 (20 mL) was added and the layers were separated. The aqueous phase was extracted with dichloromethane (20 mL) once, and the combined organic phases were dried with anhydrous sodium sulfate, filtered and concentrated. Purification by flash chromatography (dichloromethane/MeOH=40:1→10:1), afforded 1.6 g (88%) of (R)-2'-((5S,8S)-5-((E)-4-chlorobut-1-en-1-yl)-8-isopropyl-12,12-dimethyl-3,7,10-trioxo-6,11-dioxa-2,9-diazatridecyl)-4-methyl-4,5-dihydro-[2,4'-bithiazole]-4-carboxylic acid as a foam. Mass Spec(m/z): 617.9.

All published documents (e.g. patents, journal articles, books) cited herein are incorporated by reference in their entireties.

What is claimed is:
1. An alkyl chloride compound of Formula (XX)

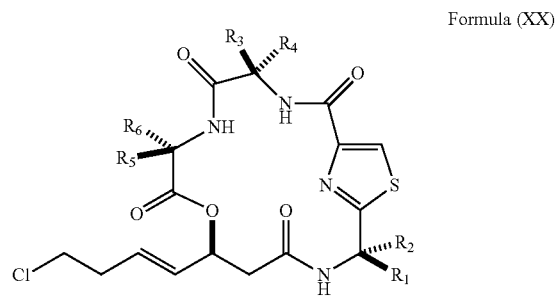

Formula (XX)

or a pharmaceutically acceptable salt thereof, wherein:
$R_1$ and $R_2$ are independently selected from the group consisting of H, $C_1$-$C_{10}$ alkyl and $C_3$-$C_7$ cycloalkyl, or $R_1$ and $R_2$ taken together with the carbon atom to which $R_1$ and $R_2$ are attached form a $_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COON, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, —$NR_8C(O)OR_9$, and —$C(O)NR_8R_9$;

$R_3$ and $R_4$ are independently selected from the group consisting of H, $C_1$-$C_{10}$ alkyl and $C_3$-$C_7$ cycloalkyl, or $R_3$ and $R_4$ taken together with the carbon atom to which $R_3$ and $R_4$ are attached form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, —$NR_8C(O)OR_9$, and —$C(O)NR_8R_9$;

$R_5$ and $R_6$ are independently selected from the group consisting of H, $C_1$-$C_{10}$ alkyl and $C_3$-$C_7$ cycloalkyl, or $R_5$ and $R_6$ taken together with the carbon atom to which $R_5$ and $R_6$ are attached form a $C_3$-$C_7$ cycloalkyl or $C_3$-$C_7$ heterocycloalkyl wherein the $C_1$-$C_{10}$ alkyl, $C_3$-$C_7$ cycloalkyl and $C_3$-$C_7$ heterocycloalkyl are optionally substituted with one or more substituents selected from the group consisting of $C_1$-$C_{10}$ alkyl, $C_3$-$C_7$ cycloalkyl, $C_3$-$C_7$ heterocycloalkyl, aryl, heteroaryl, halo, hydroxyl, —CN, —COOH, —$CF_3$, —$OCH_2F$, —$OCHF_2$, —$OC_1$-$C_{10}$ alkyl, —O-aryl, —O-heteroaryl, —$NR_8R_9$, —$NR_8C(O)R_9$, —$NR_8C(O)OR_9$, and —$C(O)NR_8R_9$;

$R_8$ and $R_9$ are independently selected from the group consisting of H, $C_1$-$C_{10}$ alkyl and $C_3$-$C_7$ cycloalkyl, wherein the $C_1$-$C_{10}$ alkyl and $C_3$-$C_7$ cycloalkyl are optionally substituted with one or more substituents selected from the group consisting $C_1$-$C_{10}$ alkyl, $_3$-$C_7$ cycloalkyl, $C_3$-$C_7$ heterocycloalkyl, aryl, heteroaryl, halo, hydroxyl, —CN, —COOH, —CF$_3$, —OCH$_2$F, —OCHF$_2$, —OC$_1$-C$_{10}$ alkyl, —O-aryl, —O-heteroaryl, —NR$_{10}$R$_{11}$, —NR$_{10}$C(O)R$_{11}$, —NR$_{10}$C(O)OR$_{11}$ and —C(O)NR$_{10}$R$_{11}$; and R$_{10}$ and R$_{11}$ are independently selected from the group consisting of H, C$_1$-C$_{10}$ alkyl and C$_3$-C$_7$ cycloalkyl.

2. The alkyl chloride compound according to claim 1, wherein R$_1$, R$_2$, R$_3$, R$_4$, R$_5$ and R$_6$ are independently H or C$_1$-C$_{10}$ alkyl.

3. The alkyl chloride compound according to claim 1, wherein:

R$_1$ and R$_2$ are H;

R$_3$ and R$_4$ are independently C$_1$-C$_{10}$ alkyl; and

R$_5$ is H and R$_6$ is C$_1$-C$_{10}$ alkyl, or R$_5$ is C$_1$-C$_{10}$ alkyl and R$_6$ is H.

4. The alkyl chloride compound according to claim 1, wherein:

R$_1$ and R$_2$ are H;

R$_3$ and R$_4$ are CH$_3$; and

R$_5$ is H and R$_6$ is isopropyl, or R$_5$ is isopropyl and R$_6$ is H.

5. The alkyl chloride compound according to claim 1 having the following structure

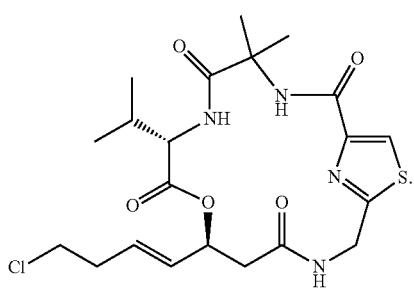 [SMILES: CC(C)[C@@H]1NC(=O)C(C)(C)NC(=O)c2csc(n2)CNC(=O)C[C@@H](/C=C/CCCl)OC1=O]

6. A method of preparing a compound of Formula (XXV)

(XXV)

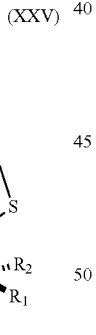

or a pharmaceutically acceptable salt thereof, comprising: treating the alkyl chloride compound according to claim 2 with a compound of Formula (XXIII)

(XXIII)

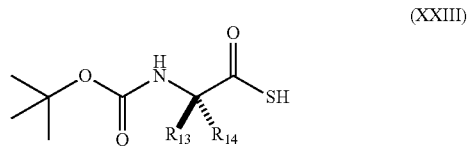

wherein R$_{13}$ is H and R$_{14}$ is C$_1$C$_{10}$ alkyl, or R$_{13}$ is C$_1$-C$_{10}$ alkyl and R$_{14}$ is H, to provide a compound of Formula (XXIV)

(XXIV)

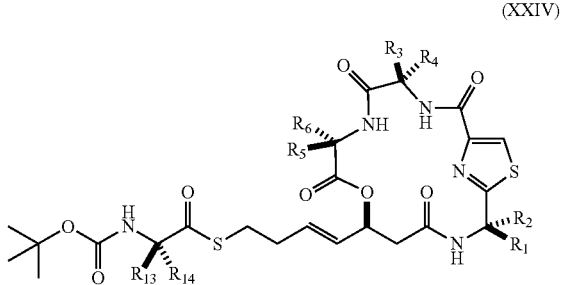

followed by deprotection of the compound of Formula XXIV to provide the compound of Formula (XXV) or a pharmaceutically acceptable salt thereof.

7. The method according to claim 6, wherein for the compound of Formula (XXV) or a pharmaceutically acceptable salt thereof, R$_1$ and R$_2$ are H;

R$_3$ and R$_4$ are independently C$_1$-C$_{10}$ alkyl; and

R$_5$ is H and R$_6$ is C$_1$-C$_{10}$ alkyl, or R$_5$ is C$_1$-C$_{10}$ alkyl and R$_6$ is H.

8. The method according to claim 7, wherein the pharmaceutically acceptable salt is a hydrochloride salt.

9. The method according to claim 7, wherein the pharmaceutically acceptable salt is benzenesulfonate salt.

* * * * *

UNITED STATES PATENT AND TRADEMARK OFFICE
CERTIFICATE OF CORRECTION

| | |
|---|---|
| PATENT NO. | : 11,739,123 B2 |
| APPLICATION NO. | : 17/340731 |
| DATED | : August 29, 2023 |
| INVENTOR(S) | : Anthony D. Piscopio et al. |

It is certified that error appears in the above-identified patent and that said Letters Patent is hereby corrected as shown below:

In the Claims

Claim 1 at Column 56, Line 32: should read -- eroaryl, halo, hydroxyl, —CN, —COOH, —CF$_3$, --

Signed and Sealed this
Third Day of October, 2023

*Katherine Kelly Vidal*

Katherine Kelly Vidal
*Director of the United States Patent and Trademark Office*